United States Patent [19]

Barner et al.

[11] Patent Number: 5,739,385
[45] Date of Patent: Apr. 14, 1998

[54] PROCESS FOR PREPARING OPTICALLY ACTIVE CARBOXYLIC ACIDS

[75] Inventors: Bruce Armin Barner, Alum Creek; Jonathan Joshua Kurland, Charleston, both of W. Va.

[73] Assignee: Union Carbide Chemicals & Plastics Technology Corporation, Danbury, Conn.

[21] Appl. No.: 545,349

[22] Filed: Oct. 19, 1995

[51] Int. Cl.$^6$ ................................................. C07C 51/16
[52] U.S. Cl. .................................... 562/418; 562/431
[58] Field of Search ................................ 562/531, 418

[56] References Cited

U.S. PATENT DOCUMENTS

| | | | |
|---|---|---|---|
| 3,925,458 | 12/1975 | Kogure | 562/418 |
| 3,965,161 | 6/1976 | Kogure | 562/418 |
| 4,885,404 | 12/1989 | Wuts | 562/418 |
| 5,072,037 | 12/1991 | Weber | 562/418 |
| 5,237,092 | 8/1993 | Tauaha . | |
| 5,286,902 | 2/1994 | James | 562/418 |
| 5,434,302 | 7/1995 | Paradies | 562/418 |

FOREIGN PATENT DOCUMENTS

| | | |
|---|---|---|
| 2040742 | 10/1991 | Canada . |
| 870846 | 3/1953 | Germany . |
| 52-073106 | 6/1977 | Japan . |
| 54-012340 | 1/1979 | Japan . |
| 59-199653 | 11/1984 | Japan . |
| 03-157345 | 7/1991 | Japan . |
| 1521906 | 8/1978 | United Kingdom . |

OTHER PUBLICATIONS

Dodd, R.H.; Le Hyaric, M. "The Oxidation of Aromatic Aldehydes to Carboxylic Acids Using Hydrogen Peroxide in Formic Acid" *Synthesis* 1993, 295.

Dodd, R.H.: Doisy, X.; Potier, P. "Synthesis and Pharmacological of a Pyrido[3',4':5,4] Pyrrolo[1,2-c]-[1,4]Benzodiazepine-3, 10-Dione, a New Benzodiazepine-. . ." *Heterocycles* 1989, 28 (2), 1101.

Choi, J.-K.; Chang, Y.-K.; Hong, S.Y. "Catalytic Oxidation of Aldehydes to Carboxylic Acids With Hydrogen Peroxide as Oxidant" *Tetrahedron Lett.* 1988, 29 (16), 1967.

Hiatt, R.R.; Glover, L.C.; Mosher, H.M. "Concerted Mechanism and Phase Effects in Decompositions of Alkyl Peroxy Esters" *J. Amer. Chem. Soc.* 1975, 97 (6), 1556.

T. Maki, "Alpha-branched Aliphatic Carboxylic Acids" *Chem. Abstr.* 90:168072g, 1979.

Larkin, D.R. "The Role of Catalysts in the Air Oxidation of Aliphatic Aldehydes" *J. Org. Chem.* 1990, 55, 1565–1568.

*Primary Examiner*—Michael L. Shippen
*Attorney, Agent, or Firm*—Gerald L. Coon

[57] ABSTRACT

This invention relates to a process for preparing optically active carboxylic acids by oxidizing an optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid. Such optically active carboxylic acids have utility for example as pharmaceuticals.

19 Claims, No Drawings

5,739,385

PROCESS FOR PREPARING OPTICALLY ACTIVE CARBOXYLIC ACIDS

BRIEF SUMMARY OF THE INVENTION

RELATED APPLICATIONS

The following are related, commonly assigned applications filed on an even date herewith: U.S. patent application Ser. No. 08/547,702 and U.S. patent application Ser. No. 08/545,308, both of which are incorporated herein by reference.

1. Technical Field

This invention relates to a process for preparing optically active carboxylic acids by oxidizing an optically active aldehyde with a peracid in the presence of an amine and/or amine N-oxide catalyst to produce the optically active carboxylic acid.

2. Background of the Invention

Asymmetric synthesis is of importance, for example, in the pharmaceutical industry, since frequently only one optically active isomer (enantiomer) is therapeutically active. An example of such a pharmaceutical product is the non-steroidal anti-inflammatory drug naproxen. The S enantiomer is a potent anti-arthritic agent while the R enantiomer is a liver toxin. It is therefore oftentimes desirable to selectively produce one particular enantiomer over its mirror image.

It is known that special precautions must be taken to ensure production of a desired enantiomer because of the tendency to produce optically inactive racemic mixtures, that is equal amounts of each mirror image enantiomer whose opposite optical activities cancel out each other, or partially optically active mixtures, that is other than equal amounts of each enantiomer which may be looked at as mixtures of the optically inactive racemic mixture and the optically ratio enantiomer which is in excess. In order to obtain the desired enantiomer (or mirror image stereoisomer) from such a racemic mixture, the racemic mixture must be separated into its optically active components. This separation, known as optical resolution, may be carried out by actual physical sorting, direct crystallization of the racemic mixture, or other methods known in the art (see, for example, U.S. Pat. No. 4,242,193). Such optical resolution procedures are often laborious and expensive as well as destructive to the desired enantiomer. Due to these difficulties, increased attention has been placed upon asymmetric synthesis in which one of the enantiomers is obtained in significantly greater amounts than the other enantiomer. Efficient asymmetric synthesis affords a high degree of control in stereoselectivity and, desirably, regioselectivity where applicable, e.g., branched/normal isomer ratio in alpha-olefin hydroformylation.

DISCLOSURE OF THE INVENTION

This invention relates to a process for producing an optically active carboxylic acid which process comprises oxidizing an optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid, wherein said amine and/or amine N-oxide catalyst has a basicity sufficient to catalyze said oxidizing of the optically active aldehyde to the optically active carboxylic acid.

This invention also relates to a process for producing an optically active carboxylic acid which process comprises: (1) reacting a prochiral or chiral compound with carbon monoxide and hydrogen in the presence of an optically active metal-ligand complex catalyst to produce an optically active aldehyde; and (2) oxidizing the optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid, wherein said amine and/or amine N-oxide catalyst has a basicity sufficient to catalyze said oxidizing of the optically active aldehyde to the optically active carboxylic acid.

This invention further relates to a process for producing an optically active carboxylic acid which process comprises: (1) reacting a prochiral or chiral olefinically unsaturated organic compound with carbon monoxide and hydrogen in the presence of an optically active rhodium-ligand complex catalyst to produce an optically active aldehyde; and (2) oxidizing the optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid, wherein said amine and/or amine N-oxide catalyst has a basicity sufficient to catalyze said oxidizing of the optically active aldehyde to the optically active carboxylic acid.

DETAILED DESCRIPTION

Forming Enantiomeric Aldehyde Mixture

This invention encompasses first providing a suitable enantiomeric aldehyde mixture. Such mixtures can be provided by such known processes as non-asymmetric processes (e.g., non-asymmetric hydroformylation, non-asymmetric olefin isomerization or non-asymmetric aldol condensation) followed by conventional resolution processes (e.g., chiral chromatography, kinetic resolution or other known resolution methods). However, the enantiomeric aldehyde mixtures are preferably provided by carrying out any known conventional non-asymmetric syntheses of aldehyde mixtures in an asymmetric fashion. In such preferred processes, the catalyst of a conventional non-asymmetric synthesis is replaced by an optically active metal-ligand complex catalyst and the process is conducted to produce a suitable optically active aldehyde mixture. Illustrative of such asymmetric processes include, for example, asymmetric hydroformylation, asymmetric olefin isomerization and asymmetric aldol condensation.

Preferably, the first step of the process of this invention comprises forming an enantiomeric aldehyde mixture by asymmetric hydroformylation. Such asymmetric hydroformylation processes involve the use of an optically active metal-phosphorus ligand complex catalyst and, optionally, free ligand to produce optically active aldehydes by reacting a prochiral or chiral olefinic compound with carbon monoxide and hydrogen. The optically active aldehydes produced in this preferred first step of the process of this invention are compounds obtained by the addition of a formyl group to an olefinically unsaturated carbon atom in the starting material with simultaneous saturation of the olefinic bond. The processing techniques of this preferred first step of the process of this invention may correspond to any of the known processing techniques heretofore employed in conventional asymmetric syntheses reactions, including asymmetric hydroformylation reactions. For instance, the asymmetric processes can be conducted in continuous, semi-continuous or batch fashion and can involve a liquid recycle operation if desired. This asymmetric hydroformylation process step is preferably conducted in batch fashion. Likewise, the manner or order of addition of the reaction ingredients, catalyst and solvent are also not critical and may be accomplished in any conventional fashion.

Alternatively, as the first step in the process of this invention, asymmetric olefin isomerization can be carried out in accordance with conventional procedures known in the art to produce the enantiomeric aldehyde mixtures used in this invention. For example, allylic alcohols can be isomerized under isomerization conditions in the presence of an optically active metal-ligand complex catalyst described herein to produce optically active aldehydes.

Also alternatively, as the first step in the process of this invention, asymmetric aldol condensation can be carried out in accordance with conventional procedures known in the art to produce the enantiomeric aldehyde mixtures used in this invention. For example, optically active aldehydes can be prepared by reacting a prochiral aldehyde and a silyl enol ether under aldol condensation conditions in the presence of an optically active metal-ligand complex catalyst described herein.

In general, the above-mentioned asymmetric synthesis processes are carried out in a liquid reaction medium that contains a solvent for the optically active catalyst, preferably one in which the reaction ingredients including catalyst are substantially soluble. In addition, it may be desired that the asymmetric processes be effected in the presence of free ligand as well as in the presence of the optically active complex catalyst. By "free ligand" is meant ligand that is not complexed with the metal atom in the optically active complex catalyst.

The prochiral and chiral starting materials useful in the processes for producing the enantiomeric aldehyde mixtures employed in the process of this invention are chosen depending on the particular asymmetric synthesis process that is used. Such starting materials are well known in the art and can be used in conventional amounts in accordance with conventional methods. Illustrative starting material reactants include, for example, substituted and unsubstituted aldehydes (for aldol condensation processes), prochiral olefins (for hydroformylation processes) and ketones (for aldol condensation processes) and the like.

Illustrative olefin starting material reactants useful in certain of the asymmetric synthesis processes for producing the enantiomeric aldehyde mixtures employed in this invention (e.g., asymmetric hydroformylation) include those which can be terminally or internally unsaturated and be of straight chain, branched-chain or cyclic structure. Such olefins can contain from 2 to 40 carbon atoms or greater and may contain one or more ethylenic unsaturated groups. Moreover, such olefins may contain groups or substituents which do not essentially adversely interfere with the asymmetric syntheses process such as carbonyl, carbonyloxy, oxy, hydroxy, oxyearbonyl, halogen, alkoxy, aryl, haloalkyl, and the like. Illustrative olefinic unsaturated compounds include substituted and unsubstituted alpha olefins, internal olefins, alkyl alkenoates, alkenyl alkanoates, alkenyl alkyl ethers, alkenols and the like, e.g., 1-butene, 1-pentene, 1-hexene, 1-octene, 1-decene, 1-dodecene, 1-octadecene, 2-butene, isoamylene, 2-pentene, 2-hexene, 3-hexene, 2-heptene, cyclohexene, propylene dimers, propylene trimers, propylene tetramers, 2-ethylhexene, 3-phenyl-1-propene, 1,4-hexadiene, 1,7-octadiene, 3-cyclohexyl-1-butene, allyl alcohol, hex-1-en-4-ol, oct-1-en-4-ol, vinyl acetate, allyl acetate, 3-butenyl acetate, vinyl propionate, allyl propionate, allyl butyrate, methyl methacrylate, 3-butenyl acetate, vinyl ethyl ether, allyl ethyl ether, n-propyl-7-octenoate, 3-butenenitrile, 5-hexenamide, styrene, norbornene, alpha-methylstyrene and the like. Illustrative preferred olefinic unsaturated compounds include, for example, p-isobutylstyrene, 2-vinyl-6-methoxynaphthylene, 3-ethenylphenyl phenyl ketone, 4-ethenylphenyl-2-thienylketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether, vinyl chloride and the like. Suitable olefinic unsaturated compounds useful in certain asymmetric syntheses processes of this invention include substituted aryl ethylenes described in U.S. Pat. No. 4,329,507, the disclosure of which is incorporated herein by reference. Mixtures of different olefinic starting materials can be employed, if desired, in the asymmetric syntheses processes used as the first step in the process of this invention. More preferably, the first step involves hydroformylating alpha olefins containing from 4 to 40 carbon atoms or greater and internal olefins containing from 4 to 40 carbon atoms or greater or mixtures of such alpha olefins and internal olefins.

Illustrative prochiral and chiral olefins useful in the processes that can be employed to produce the enantiomeric aldehyde mixtures that can be employed in this invention include those represented by the formula:

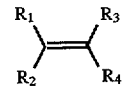

wherein $R_1$, $R_2$, $R_3$ and $R_4$ are the same or different (provided $R_1$ is different from $R_2$ or $R_3$ is different from $R_4$) and are selected from hydrogen; alkyl; substituted alkyl, said substitution being selected from dialkylamino such as benzylamino and dibenzylamino, alkoxy such as methoxy and ethoxy, acyloxy such as acetoxy, halo, nitro, nitrile, thio, carbonyl, carboxamide, carboxaldehyde, carboxyl, carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, halo, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R-groups are connected to form ring compounds, e.g., 3-methyl-1-cyclohexene, and the like.

The optically active catalyst useful in producing the aldehyde mixtures that are employed in this invention includes an optically active metal-ligand complex catalyst in which the ligand is optically active, preferably optically pure. The permissible metals which make up the optically active metal-ligand complexes include Group VIII metals selected from rhodium (Rh), cobalt (Co), iridium (It), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium and ruthenium, especially rhodium. Other permissible metals include Group IB metals selected from copper (Cu), silver (Ag), gold (Au) and mixtures thereof, and also Group VIB metals selected from chromium (Cr), molybdenum (Mo), tungsten (W) and mixtures thereof, and also Group VA metals selected from arsenic (As) and antimony (Sb) and mixtures thereof. Mixtures of metals from Group VIII, Group IB, Group VIB and Group VA may be used in this invention. It is to be noted that the successful practice of this invention does not depend and is not predicated on the exact structure of the optically active metal-ligand complex species, which may be present in their mononuclear, dinuclear and or higher nuclearity forms, provided the ligand is optically active. Indeed, the exact optically active structure is not known. Although it is not intended herein to be bound to any theory or mechanistic discourse, it appears that the optically active catalytic species may in its simplest form consist essentially of the metal in complex combination with the optically active ligand and, in hydroformylation, carbon monoxide, hydrogen and an olefin.

The term "complex" as used herein and in the claims means a coordination compound formed by the union of one or more electronically rich molecules or atoms capable of independent existence with one or more electronically poor molecules or atoms, each of which is also capable of independent existence. For example, the preferred optically active ligands employable herein, i.e., phosphorus ligands, may possess one or more phosphorus donor atoms, each having one available or unshared pair of electrons which are each capable of forming a coordinate covalent bond independently or possibly in concert (e.g., via chelation) with the metal. As can be surmised from the above discussions, carbon monoxide (which is also properly classified as ligand) can also be present and complexed with the metal. The ultimate composition of the optically active complex catalyst may also contain an additional ligand, e.g., hydrogen or an anion satisfying the coordination sites or nuclear charge of the metal. Illustrative additional ligands include, e.g., halogen (Cl, Br, I), alkyl, aryl, substituted aryl, acyl, $CF_3$, $C_2F_5$, CN, $R_2PO$ and $RP(O)(OH)O$ (wherein each R is alkyl or aryl), acetate, acetylacetonate, $SO_4$, $PF_4$, $PF_6$, $NO_2$, $NO_3$, $CH3O$, $CH_2=CHCH_2$, $C_6H_5CN$, $CH_3CN$, NO, $NH_3$, pyridine, $(C_2H_5)_3N$, mono-olefins, diolefins and triolefins, tetrahydrofuran, and the like. It is of course to be understood that the optically active complex species is preferably free of any additional organic ligand or anion that might poison the catalyst and have an undue adverse effect on catalyst performance. It is preferred in the rhodium-catalyzed asymmetric hydroformylation reactions of this invention that the active catalysts be free of halogen and sulfur directly bonded to the rhodium, although such may not be absolutely necessary.

The number of available coordination sites on such metals is well known in the art. Thus the optically active species may comprise a complex catalyst mixture, in their monomeric, dimeric or higher nuclearity forms, which are preferably characterized by at least one phosphorus-containing molecule complexed per one molecule of rhodium. As noted above, it is considered that the optically active species of the preferred rhodium catalyst employed in this invention during asymmetric hydroformylation may be complexed with carbon monoxide and hydrogen in addition to the optically active phosphorus ligands in view of the carbon monoxide and hydrogen gas employed by the asymmetric hydroformylation process.

Moreover, regardless of whether the optically active complex catalyst is formed prior to introduction into the reaction zone or whether the active catalyst is prepared in situ during the reaction, the asymmetric synthesis processes (and especially the asymmetric hydroformylation processes) may, if desired, be effected in the presence of free ligand.

The ligands employable in producing the enantiomeric aldehyde mixtures useful in this invention include those optically active ligands having the general formula:

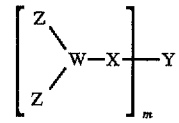

wherein each W is the same or different and is phosphorus, arsenic or antimony, each X is the same or different and is oxygen, nitrogen or a covalent bond linking W and Y, Y is an m-valent substituted or unsubstituted hydrocarbon residue, each Z is the same or different and is a substituted or unsubstituted hydrocarbon residue, preferably a hydrocarbon residue containing at least one heteroatom which is bonded to W, or the Z substituents bonded to W may be bridged together to form a substituted or unsubstituted cyclic hydrocarbon residue, preferably a cyclic hydrocarbon residue containing at least 2 heteroatoms which are each bonded to W, and m is a value equal to the free valence of Y, preferably a value of from 1 to 6, provided at least one of Y and Z is optically active.

Referring to the above general formula, it is appreciated that when m is a value of 2 or greater, the ligand may include any combination of permissible cyclic hydrocarbon residues and/or acyclic hydrocarbon residues which satisfy the valence of Y. It is also appreciated that the hydrocarbon residues represented by Z may include one or more heteroatoms and such heteroatom may be directly bonded to W. The optically active ligands included in the above general structure should be easily ascertainable by one skilled in the art.

Illustrative optically active ligands employable in the first step of the processes this invention include those of the formulae:

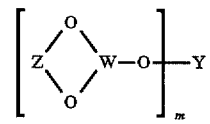

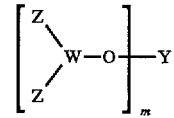

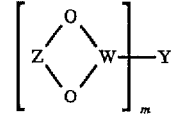

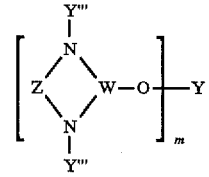

wherein W, Y, Z and m are as defined hereinabove and Y''' is the same or different and is hydrogen or a substituted or unsubstituted hydrocarbon residue. Illustrative preferred optically active ligands encompassed by the above formulae include, for example, (poly)phosphites, (poly)phosphinites, (poly)phosphonites and the like.

Illustrative preferred optically active ligands employable in this invention include the following:

(i) optically active polyphosphites having the formula:

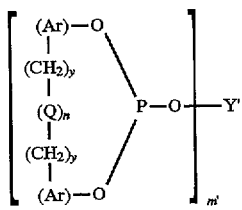

wherein each Ar group is the same or different and is a substituted or unsubstituted aryl radical; Y' is an m-valent substituted or unsubstituted hydrocarbon radical selected from alkylene, alkylene-oxy- alkylene, arylene and arylene-$(CH_2)_y$—$(Q)_n$—$(CH_2)_y$— arylene; each y is the same or different and is a value of 0 or 1; each n is the same or different and is a value of 0 or 1; each Q is the same or different and is a substituted or unsubstituted divalent bridging group selected from —$CR^1R^2$—, —O—, —S—, —$NR^3$—, —$SiR^4R^5$— and —CO—, wherein $R^1$ and $R^2$ are the same or different and are hydrogen or a substituted or unsubstituted radical selected from alkyl of 1 to 12 carbon atoms, phenyl, tolyl and anisyl, and $R^3$, $R^4$ and $R^5$ are the same or different and are a radical selected from hydrogen or methyl; and m' is a value of from 2 to 6;

(ii) optically active diorganophosphites having the formula:

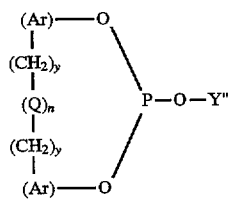

wherein Y" is a substituted or unsubstituted monovalent hydrocarbon radical, and Ar, Q, n and y are as defined above; and (iii) optically active open-ended bisphosphites having the formula:

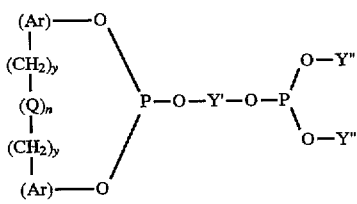

wherein Ar, Q, n, y, Y' and Y" are as defined above and Y'" can be the same or different.

Illustrative aryl radicals of the Ar and Y' groups of the above formulae include aryl moieties which may contain from 6 to 18 carbon atoms such as phenylene, naphthylene, anthracylene and the like. In the above formulae, preferably m is from 2 to 4 and each y and each n has a value of 0. However, when n is 1, Q preferably is a —$CR^1R^2$— bridging group as defined above and more preferably methylene (—$CH_2$—) or alkylidene (—$CHR^2$—), wherein $R^2$ is an alkyl radical of 1 to 12 carbon atoms (e.g., methyl, ethyl, propyl, isopropyl, butyl, dodecyl, etc.), especially methyl.

The m-valent hydrocarbon radicals represented by Y' in the polyphosphite ligand formula above are hydrocarbons containing from 2 to 30 carbon atoms selected from alkylene, alkylene-oxy-alkylene, arylene, and arylene-(—$CH_2$—)$_y$—$(Q)_n$—(—$CH_2$—)$_y$— arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

The divalent bridging group represented by Y' in the open-ended bisphosphite ligand formula above are divalent hydrocarbons containing from 2 to 30 carbon atoms selected from alkylene, alkylene-oxy-alkylene, arylene and arylene-(—$CH_2$—)$_y$—$(Q)_n$— (—$CH_2$—)$_y$-arylene radicals, wherein Q, n and y are the same as defined above. Preferably the alkylene moieties of said radicals contain from 2 to 18 carbon atoms and more preferably from 2 to 12 carbon atoms, while the arylene moieties of said radicals preferably contain from 6 to 18 carbon atoms.

Hydrocarbon radicals represented by Y" in the above phosphite ligand formulae include monovalent hydrocarbon radicals containing from 1 to 30 carbon atoms selected from alkyl radicals including linear or branched primary, secondary or tertiary alkyl radicals, such as methyl, ethyl, n-propyl, isopropyl, amyl, sec-amyl, t-amyl, 2-ethylhexyl and the like; aryl radicals such as phenyl, naphthyl and the like; aralkyl radicals such as benzyl, phenylethyl, tri-phenylmethylethane and the like; alkaryl radicals such as tolyl, xylyl and the like; and cycloalkyl radicals such as cyclopentyl, cyclohexyl, cyclohexylethyl and the like. Preferably, Y" is selected from alkyl and aryl radicals which contain from about 1 and 30 carbon atoms. Preferably, the alkyl radicals contain from 1 to 18 carbon atoms, most preferably from 1 to 10 carbon atoms, while the aryl, aralkyl, alkaryl and cycloalkyl radicals preferably contain from 6 to 18 carbon atoms. Further, although each Y" group in the open-ended bisphosphite ligand formula above may differ from the other, preferably they are identical.

The aryl radicals in the above formulae may also be substituted with any substituent radical that does not unduly adversely affect the processes of this invention. Illustrative substituents include radicals containing from 1 to 18 carbon atoms such as alkyl, aryl, aralkyl, alkaryl and cycloalkyl radicals; alkoxy radicals; silyl radicals such as —$Si(R^9)_3$ and —$Si(OR^9)_3$; amino radicals such as —$N(R^9)_2$; acyl radicals such as —$C(O)R^9$; acyloxy radicals such as —$OC(O)R^9$; carbonyloxy radicals such as —$COOR^9$; amido radicals such as —$C(O)N(R^9)_2$ and —$N(R^9)COR^9$; sulfonyl radicals such as —$SO_2R^9$; sulfinyl radicals such as —$SOR^9$; sulfenyl radicals such as —$SR^9$; phosphonyl radicals such as —$P(O)(R^9)_2$; as well as halogen, nitro, cyano, trifluoromethyl and hydroxy radicals and the like, wherein each $R^9$ can be a monovalent hydrocarbon radical such as alkyl, aryl, alkaryl, aralkyl and cycloalkyl radicals, with the provisos that in amino substitutents such as —$N(R^9)_2$, each $R^9$ taken together can also comprise a divalent bridging group that forms a heterocyclic radical with the nitrogen atom, in amido substituents such as —$C(O)N(R^9)_2$ and —$N(R^9)COR^9$, each $R^9$ bonded to N can also be hydrogen, and in phosphonyl substituents such as —$P(O)(R^9)_2$, one $R^9$ can be hydrogen. It is to be understood that each $R^9$ group in a particular substituent may be the same of different. Such hydrocarbon substituent radicals could possibly in turn be substituted with a substituent such as already herein outlined above provided that any such occurrence would not unduly adversely effect the processes of this invention. At least one ionic moiety selected from salts of carboxylic acid and of sulfonic acid may be substituted on an aryl moiety in the above formulae.

Among the more preferred phosphite ligands useful in the first step in the process of this invention are those ligands wherein the two Ar groups linked by the bridging group represented by —$(CH_2)_y$—$(Q)_n$—$(CH_2)_y$— in the above formulae are bonded through their ortho positions in relation to the oxygen atoms that connect the Ar groups to the phosphorus atom. It is also preferred that any substituent radical, when present on such Ar groups, be bonded in the para and/or ortho position on the aryl in relation to the oxygen atom that bonds the substituted Ar group to its phosphorus atom.

Illustrative monovalent hydrocarbon residues represented by the Z, Y, Y" and Y'" groups in the above formulae include substituted or unsubstituted monovalent hydrocarbon radicals containing from 1 to 30 carbon atoms selected from substituted or unsubstituted alkyl, aryl, alkaryl, aralkyl and alicyclic radicals. While each Z and Y" group in a given formula may be individually the same or different, preferably they are both the same. More specific illustrative monovalent hydrocarbon residues represented by Z, Y, Y" and Y'" include primary, secondary and tertiary chain alkyl radicals such as methyl, ethyl, propyl, isopropyl, butyl, sec-butyl, t-butyl, neo-pentyl, sec-amyl, t-amyl, iso-octyl, 2-ethylhexyl, iso-nonyl, iso-decyl, octadecyl and the like; aryl radicals such as phenyl, naphthyl, anthracyl and the like; aralkyl radicals such as benzyl, phenylethyl and the like; alkaryl radicals such as tolyl, xylyl, p-alkylphenyls and the like; and alicyclic radicals such as cyclopentyl, cyclohexyl, cyclooctyl, cyclohexylethyl, 1-methylcyclohexyl and the like. Preferably the unsubstituted alkyl radicals may contain from 1 to 18 carbon atoms, more preferably from 1 to 10 carbon atoms, while the unsubstituted aryl, aralkyl, alkaryl and alicyclic radicals preferably contain from 6 to 18 carbon atoms. Among the more preferred Z, Y, Y" and Y'" residues are phenyl and substituted phenyl radicals.

Illustrative divalent hydrocarbon residues represented by Z, Y and Y' in the above formulae include substituted and unsubstituted radicals selected from alkylene, -alkyleneoxy-alkylene, arylene, -arylene-oxy-arylene-, alicyclic radicals, phenylene, naphthylene, -arylene-$(CH_2)_y(Q)_n(CH_2)_y$-arylene- such as -phenylene-$(CH2)y(Q)n(CH2)y$-phenylene- and -naphthylene-$(CH_2)_y(Q)_n(CH_2)_y$-naphthylene-radicals, wherein Q, y and n are as defined hereinabove. More specific illustrative divalent radicals represented by Z, Y and Y' include, e.g., 1,2-ethylene, 1,3-propylene, 1,6-hexylene, 1,8-octylene, 1,12-dodecylene, 1,4-phenylene, 1,8-naphthylene, 1,1'-biphenyl-2,2'-diyl, 1,1'-binaphthyl-2,2'-diyl, 2,2'-binaphthyl-1,1-diyl and the like. The alkylene radicals may contain from 2 to 12 carbon atoms, while the arylene radicals may contain from 6 to 18 carbon atoms. Preferably Z is an arylene radical, Y is an alkylene radical and Y' is an alkylene radical.

Moreover, the above-described radicals represented by Z, Y, Ar, Y' and Y" of the above formulae, may be further substituted with any substituent that does not unduly adversely effect the desired results of this invention. Illustrative substituents are, for example, monovalent hydrocarbon radicals having between one and about 18 carbon atoms, such as alkyl, aryl, alkaryl, aralkyl, cycloalkyl and other radicals as defined above. In addition, various other substituents that may be present include, e.g., halogen, preferably chlorine or fluorine, —$NO_2$, —CN, —$CF_3$, —OH, —$Si(CH_3)3$, —$Si(OCH3)_3$, —$Si(C_3H_7)_3$, —$C(O)CH_3$, —$C(O)C_2H_5$, —$OC(O)C6H_5$, —$C(O)OCH_3$, —$N(CH_3)_2$, —$NH_2$, —$NHCH_3$, —$NH(C_2H_5)$, —$CONH_2$, —$CON(CH_3)_2$, —$S(O)_2C_2H_5$, —$OCH_3$, —$OC_2H_5$, —$OC_6H_5$, —$C(O)C_6H_5$, —$O(t-C_4H_9)$, —$SC_2H_5$, —$OCH_2CH_2OCH_3$, —$(OCH_2CH_2)_2OCH_3$, —$(OCH_2CH_2)_3OCH_3$, —$SCH_3$, —$S(O)CH_3$, —$SC_6H_5$, —$P(O)(C_6H_5)_2$, —$P(O)(CH_3)_2$, —$P(O)(C_2H_5)_2$, —$P(O)(C_3H_7)_2$, —$P(O)(C_4H_9)_2$, —$P(O)(C_6H_{13})_2$, —$P(O)CH_3(C_6H_5)$, —$P(O)(H)(C_6H_5)$, —$NHC(O)CH_3$ and the like. Moreover, each Z, Y, Ar, Y' and Y" group may contain one or more such substituent groups which may also be the same or different in any given ligand molecule. Preferred substituent radicals include alkyl and alkoxy radicals containing from 1 to 18 carbon atoms and more preferably from 1 to 10 carbon atoms, especially t-butyl and methoxy.

The optically active ligands employed in the complex catalysts useful in the first step of the process of this invention are uniquely adaptable and suitable for asymmetric syntheses processes, especially rhodium-catalyzed asymmetric hydroformylation. For instance, the optically active phosphorus ligands may provide very good rhodium complex stability in addition to providing good catalytic activity for the asymmetric hydroformylation of all types of permissible olefins. Further, their unique chemical structure should provide the ligand with very good stability against side reactions such as being hydrolyzed during asymmetric hydroformylation, as well as upon storage.

The types of optically active ligands of the generic class employable in the first step of the process of this invention can be prepared by methods known in the art. For instance, the optically active phosphorus ligands employable in this invention can be prepared via a series of conventional phosphorus halide-alcohol or amine condensation reactions in which at least one of the alcohol or amine ingredients is optically active or optically pure. Such types of condensation reactions and the manner in which they may be conducted are well known in the art. Moreover, the phosphorus ligands employable herein can be readily identified and characterized by conventional analytical techniques, such as Phosphorus-31 nuclear magnetic resonance spectroscopy and Fast Atom Bombardment Mass Spectroscopy if desired.

As noted above, the optically active ligands can be employed as both the ligand of the above-described optically active metal-ligand complex catalyst as well as the free ligand that can be present in the reaction medium of the processes of this invention. In addition, while the optically active ligand of the metal-ligand complex catalyst and any excess free ligand preferably present in a given process of this invention are normally the same ligand, different optically active ligands, as well as mixtures of two or more different optically active ligands, may be employed for each purpose in any given process.

The optically active metal-ligand complex catalysts of this invention may be formed by methods known in the art. See, for example, U.S. Pat. Nos. 4,769,498, 4,717,775, 4,774,361, 4,737,588, 4,885,401, 4,748,261, 4,599,206, 4,668,651, 5,059,710 and 5,113,022, all of which are incorporated herein by reference. For instance, preformed metal hydrido-carbonyl catalysts may possibly be prepared and introduced into the reaction medium of an asymmetric syntheses process. More preferably, the metal-ligand complex catalysts of this invention can be derived from a metal catalyst precursor which may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction medium along with the ligand for the in situ formation of the active catalyst. In a preferred embodiment, rhodium dicarbonyl acetylacetonate is employed as a rhodium precursor and reacted in the presence of a solvent with a phosphorus ligand compound to form a catalytic rhodium-phosphorus complex precursor which is introduced into the reactor, optionally along with excess free phosphorus ligand, for the in situ formation of the active catalyst. In any event, it is sufficient for the purpose of this invention to understand that an optically active metal-ligand complex catalyst is present in the reaction medium under the conditions of the asymmetric syntheses and more preferably asymmetric hydroformylation process.

Moreover, the mount of optically active complex catalyst present in the reaction medium need only be that minimum amount necessary to provide the given metal concentration desired to be employed and which will furnish the basis for at least that catalytic amount of metal necessary to catalyze the particular asymmetric syntheses process desired. In general, metal concentrations in the range of from about 1 ppm to about 10,000 ppm, calculated as free metal, and ligand to metal mole ratios in the catalyst ranging from about 0.5:1 to about 200:1, should be sufficient for most asymmetric syntheses processes. Moreover, in the rhodium catalyzed asymmetric hydroformylation processes of this invention, it is generally preferred to employ from about 10 to 1000 ppm of rhodium and more preferably from 25 to 750 ppm of rhodium, calculated as free metal.

A further aspect of the first step of the process of this invention involves the use of a catalyst precursor composition consisting essentially of a solubilized metal-ligand complex precursor catalyst, an organic solvent and free ligand. Such precursor compositions may be prepared by forming a solution of a metal starting material, such as a metal oxide, hydride, carbonyl or salt e.g., a nitrate, which may or may not be in complex combination with an optically active ligand, an organic solvent and a free ligand as defined herein. Any suitable metal starting material may be employed, e.g., rhodium dicarbonyl acetylacetonate, $Rh_2O_3$, $Rh_4(CO)_{12}$, $Rh_6(CO)_{16}$, $Rh(NO_3)_3$, polyphosphite rhodium carbonyl hydrides, iridium carbonyl, poly-phosphite iridium carbonyl hydrides, osmium halide, chlorosmic acid, osmium carbonyls, palladium hydride, palladous halides, platinic add, platinous halides, ruthenium carbonyls, as well as other salts of other metals and carboxylates of $C_2$-$C_{16}$ acids such as cobalt chloride, cobalt nitrate, cobalt acetate, cobalt octoate, ferric acetate, ferric nitrate, nickel fluoride, nickel sulfate, palladium acetate, osmium octoate, iridium sulfate, ruthenium nitrate, and the like. Of course, any suitable solvent may be employed such as those employable in the asymmetric syntheses process desired to be carried out. The desired asymmetric syntheses process may of course also dictate the various amounts of metal, solvent and optically active ligand present in the precursor solution. Optically active ligands if not already complexed with the initial metal may be complexed to the metal either prior to or in situ during the asymmetric syntheses process.

The optically active catalyst used in the first step of the process of this invention may optionally be supported. Advantages of a supported catalyst may include ease of catalyst separation and ligand recovery. Illustrative examples of supports include alumina, silica gel, ion-exchange resins, polymeric supports and the like.

The process conditions employable in the asymmetric processes that can be employed in the first step of the process of this invention are chosen depending on the particular asymmetric synthesis process. Such process conditions are well known in the art. All of the asymmetric syntheses processes useful in this invention can be carried out in accordance with conventional procedures known in the art. Illustrative reaction conditions for conducting the asymmetric syntheses processes of this invention are described, for example, in Bosnich, B., Asymmetric Catalysis, Martinus Nijhoff Publishers, 1986 and Morrison, James D., Asymmetric Synthesis, Vol. 5, Chiral Catalysis, Academic Press, Inc., 1985, both of which are incorporated herein by reference. Depending on the particular process, operating temperatures can range from about −80° C. or less to about 500° C. or greater and operating pressures can range from about 1 psig or less to about 10,000 psig or greater.

The reaction conditions for effecting the preferred asymmetric hydroformylation process that can be employed in the first step of the process of this invention may be those heretofore conventionally used and may comprise a reaction temperature of from about −25° C. or lower to about 200° C. and pressures ranging from about 1 to 10,000 psia. While the preferred asymmetric syntheses process is the hydroformylation of olefinically unsaturated compounds carbon monoxide and hydrogen to produce optically active aldehydes, it is to be understood that the optically active metal-ligand complexes may be employed as catalysts in other types of asymmetric syntheses processes to obtain good results.

As noted, the first step of the preferred process of this invention involves the production of optically active aldehydes via asymmetric hydroformylation of a prochiral or chiral olefinic unsaturated compound with carbon monoxide and hydrogen in the presence of an optically active metal-phosphorus ligand complex catalyst and, optionally, free phosphorus ligand, especially an optically active rhodium-phosphorus ligand complex catalyst.

While the optimization of the reaction conditions necessary to achieve the best results and efficiency desired are dependent upon experience in the utilization of this invention, only a certain measure of experimentation should be necessary to ascertain those conditions which are optimum for a given situation and such should be well within the knowledge of one skilled in the art and easily obtainable by following the more preferred aspects of this invention as explained herein and/or be simple routine experimentation. For instance, the total gas pressure of hydrogen, carbon monoxide and olefinic unsaturated starting compound of the preferred asymmetric hydroformylation process of this invention may range from about I to about 10,000 psia. More preferably, however, in the asymmetric hydroformylation of prochiral olefins to produce optically active aldehydes, it is preferred that the process be operated at a total gas pressure of hydrogen, carbon monoxide and olefinic unsaturated starting compound of less than about 1500 psia, and more preferably less than about 1000 psia. The minimum total pressure of the reactants is not particularly critical and is limited predominately only by the amount of reactants necessary to obtain a desired rate of reaction. More specifically, the carbon monoxide partial pressure of the asymmetric hydroformylation process of this invention is preferably from about 1 to about 360 psia, and more preferably from about 3 to about 270 psia, while the hydrogen partial pressure is preferably about 15 to about 480 psia and more preferably from about 30 to about 300 psia. In general, the molar ratio of gaseous hydrogen to carbon monoxide may range from about 1:10 to 100:1 or higher, the more preferred hydrogen to carbon monoxide molar ratio being from about 1:1 to about 1:10. Higher molar ratios of carbon monoxide to gaseous hydrogen may generally tend to favor higher branched/normal isomer ratios.

Further as noted above, the preferred asymmetric hydroformylation process useful in the first step of the process of this invention may be conducted at a reaction temperature from about −25° C. or lower to about 200° C. The preferred reaction temperature employed in a given process will of course be dependent upon the particular olefinic starting material and optically active metal-ligand complex catalyst employed as well as the efficiency desired. Lower reaction temperatures may generally tend to favor higher enantiomeric excesses (ee) and branched/normal ratios. In general, asymmetric hydroformylations at reaction temperatures of about 0° C. to about 120° C. are preferred for all types of olefinic starting materials. More preferably, alpha-olefins can be effectively hydroformylated at a temperature of from about 0° C. to about 90° C. while even less reactive olefins than conventional linear alpha-olefins and internal olefins as well as mixtures of alpha-olefins and internal olefins are effectively and preferably hydroformylated at a temperature of from about 25° C. to about 120° C. Indeed, in the rhodium-catalyzed asymmetric hydroformylation process of this invention, no substantial benefit is seen in operating at reaction temperatures much above 1200°0 C. and such is considered to be less desirable.

The processes employed in the first step of the process of this invention are conducted for a period of time sufficient to produce an enantiomeric aldehyde mixture. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

The asymmetric synthesis processes, preferably asymmetric hydroformylation processes, useful as the first step in the process of this invention can be carried out in either the liquid or gaseous state and involve a batch, continuous liquid or gas recycle system or combination of such systems. A batch system is preferred for conducting such processes. Preferably, such asymmetric hydroformylation involves a batch homogeneous catalysis process wherein the hydroformylation is carried out in the presence of both free phosphorus ligand and any suitable conventional solvent as further described herein.

The asymmetric synthesis processes, and preferably asymmetric hydroformylation process, useful as the first step in the process of this invention may be conducted in the presence of an organic solvent for the optically active metal-ligand complex catalyst. Depending on the particular catalyst and reactants employed, suitable organic solvents include, for example, alcohols, alkanes, alkenes, alkynes, ethers, aldehydes, ketones, esters, acids, amides, amines, aromatics and the like. Any suitable solvent which does not unduly adversely interfere with the intended asymmetric synthesis process can be employed and such solvents may include those heretofore commonly employed in known metal catalyzed processes. Increasing the dielectric constant or polarity of a solvent may generally tend to favor increased reaction rates and selectivity. Mixtures of one or more different solvents may be employed if desired. The amount of solvent employed is not critical to this invention and need only be that amount sufficient to provide the reaction medium with the particular metal, substrate and product concentration desired for a given process. In general, the amount of solvent when employed may range from about 5 percent by weight up to about 95 percent by weight or more based on the total weight of the reaction medium.

As noted above, the metal-ligand-catalyzed asymmetric synthesis processes (and especially the asymmetric hydroformylation process) useful as the first step in the process of this invention can be carried out in the presence of free ligand, i.e., ligand that is not complexed with the metal of the optically active metal-ligand complex catalyst employed. While it is preferred to employ a free ligand that is the same as the ligand of the metal-ligand complex catalyst such ligands need not be the same in a given process, but can be different if desired. While the asymmetric syntheses and preferably asymmetric hydroformylation process may be carried out in any excess amount of free ligand desired, the employment of free ligand may not be absolutely necessary. Accordingly, in general, amounts of ligand of from about 2 to about 100, or higher if desired, moles per mole of metal (e.g., rhodium) present in the reaction medium should be suitable for most purposes, particularly with regard to rhodium catalyzed hydroformylation; said amounts of ligand employed being the sum of both the amount of ligand that is bound (complexed) to the metal present and the amount of free (non-complexed) ligand present. Of course, if desired, make-up ligand can be supplied to the reaction medium of the asymmetric hydroformylation process, at any time and in any suitable manner, to maintain a predetermined level of free ligand in the reaction medium.

The ability to carry out the processes useful as the first step of the process of this invention in the presence of free ligand can be a beneficial aspect of this invention in that it removes the criticality of employing very low precise concentrations of ligand that may be required of certain complex catalysts whose activity may be retarded when even any amount of free ligand is also present during the process, particularly when large scale commercial operations are involved, thus helping to provide the operator with greater processing latitude.

As indicated above, the aldehyde-forming processes useful in this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone. The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The aldehyde-forming processes useful as the first step in the process of this invention are useful for preparing mixtures of substituted optically active aldehydes. The aldehyde-forming processes useful in this invention stereoselectively produce a chiral center. Illustrative optically aldehydes prepared by the processes of this invention include, for example, substituted aldehydes. Illustrative preferred optically active aldehyde compounds prepared by the asymmetric hydroformylation process of this invention include, for example, S-2-(p-isobutylphenyl) propionaldehyde, S-2-(6-methoxy-2-naphthyl) propionaldehyde, S-2-(3-benzoylphenyl)-propionaldehyde, S-2-(p-thienoylphenyl)propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(2-methylacetaldehyde)-5-benzoylthiophene and the like. Illustrative of suitable optically active aldehyde (including derivatives of the optically active aldehydes) and prochiral and chiral starting material compounds include those permissible optically active aldehyde and prochiral and chiral starting material compounds which are described in Kirk-Othmer, Encyclopedia of Chemical Technology, Third Edition, 1984, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The aldehyde-forming processes useful as the first step in the process of this invention can provide optically active aldehydes having very high enantioselectivity and regioselectivity. Enantiomeric excesses of preferably greater than 50%, more preferably greater than 75% and most preferably greater than 90% can be obtained by such processes. Branched/normal molar ratios of preferably greater than 5:1, more preferably greater than 10:1 and most preferably greater than 25:1 can be obtained by such processes.

In the process of this invention, the aldehyde mixtures may be separated from the other components of the crude reaction mixtures in which the aldehyde mixtures are produced by any suitable method. Suitable separation methods include, for example, solvent extraction, crystallization, distillation, vaporization, wiped film evaporation, failing film evaporation and the like. It may be desired to remove the optically active products from the crude reaction mixture as they are formed through the use of trapping agents as described in published Patent Cooperation Treaty Patent Application WO 88/08835. A preferred method for separating the enantiomeric aldehyde mixtures from the other components of the crude reaction mixtures is by membrane separation. Such membrane separation can be achieved as set out in U.S. Pat. No. 5,430,194 and copending U.S. patent application Ser. No. 08/430,790, filed May 5, 1995, both incorporated herein by reference.

In the process of this invention, the enantiometric purity of mixtures of optically active aldehyde isomers may be improved by crystallization as described in said U.S. Pat. No. 5,430,194.

The generic scope of this invention includes a process for preparing optically active carboxylic adds by oxidizing an optically active aldehyde with a peracid in the presence of an amine and/or amine N-oxide catalyst to produce the optically active carboxylic acid. The generic scope of this invention is not intended to be limited in any manner by any particular reaction for forming enantiomeric aldehyde mixtures.

Oxidation

Once the requisite mixture of enantiomeric aldehydes has been provided, the next step of the process of this invention involves oxidizing the optically active aldehyde with a peracid in the presence of an amine and/or amine N-oxide catalyst to produce an optically active carboxylic acid. Suitable solutions can be provided by using liquid aldehydes or by melting solid aldehydes. However, suitable solutions usually consist of the aldehydes dissolved in an appropriate solvent (e.g., in the solvent in which the first step of the process of this invention was conducted). Any solvent which will dissolve the aldehyde mixture and is unreactive with peracids may be used. Examples of suitable solvents are ketones (e.g., acetone), esters (e.g., ethyl acetate), hydrocarbons (e.g., toluene), nitrohydrocarbons (e.g., nitrobenzene), ethers (e.g., tetrahydrofuran (THF) and 1,2-dimethoxyethane) and water. A mixture of two or more solvents can be employed to maximize the purity and yield of the desired aldehyde. The solution used may also contain materials present in the crude reaction product of the aldehyde-forming reaction (e.g., catalyst, ligand and heavies). Preferably, however, the solution consists essentially of only the aldehyde and the solvent. The concentration of the aldehyde in the solvent solution will be limited by the solubility of the aldehyde in the solvent.

The oxidizing agent useful in the process of this invention is a peracid. Illustrative peracids include, for example, peracetic acid, performic acid, perpropionic acid, perbenzoic acid and the like. The preferred oxidizing agent is anhydrous peracetic acid. Such peracid oxidizing agents are well known in the art and can be used in amounts described below and in accordance with conventional methods.

The oxidizing agent is employed in an amount sufficient to permit complete oxidation of the optically active aldehyde. Preferably, the oxidizing agent stoichiometry can range from about 1 to about 10 molar equivalents with respect to optically active aldehyde, preferably from about 1 to about 2 molar equivalents with respect to optically active aldehyde, and most preferably from about 1 to about 1.3 molar equivalents with respect to optically active aldehyde.

The catalysts useful in the oxidation step of the process of this invention include primary, secondary and tertiary amines and amine N-oxides and mixtures thereof. The catalysts have sufficient basicity to catalyze the oxidation of an optically active aldehyde to an optically active carboxylic acid. The catalysts are desirable in that little or no racemization of the optically active aldehyde occurs. Illustrative primary, secondary and tertiary amine and amine N-oxide catalysts include, for example, aliphatic amines, aliphatic amine N-oxides, aromatic amines, aromatic amine N-oxides, heterocyclic amines, heterocyclic amine N-oxides, supported polymeric amines, supported polymeric amine N-oxides and the like, including mixtures thereof. Illustrative aliphatic amines include substituted and unsubstituted alkyl amines such as butylamine, diethylamine, triethylamine and the like including the N-oxides thereof. Illustrative aromatic amines (those in which nitrogen is attached directly to an aromatic ting) include substituted and unsubstituted anilines and the N-oxides thereof, e.g., aniline, toluidine, diphenylamine, N-ethyl-N-methylaniline, 2,4,6-tribromoaniline and the like. Illustrative heterocyclic amines (those in which nitrogen makes up a part of an aromatic or non-aromatic ring) include substituted and unsubstituted pyridines, pyrimidines, pyrrolidines, piperidines, pyrroles, purines and the like including the N-oxides thereof. Preferred oxidation catalysts include, for example, 2,6-lutidine N-oxide, 4-methoxypyridine N-oxide and 2,5-lutidine N-oxide. Amine N-oxide catalysts are preferred oxidation catalysts and can affect, e.g., decrease, the amount of formate byproduct formed in the oxidation process of this invention. The amine and/or amine N-oxide catalyst preferably has a high boiling point so as to reduce or eliminate amine impurities resulting from the catalyst in the product.

As indicated above, the catalysts have sufficient basicity to catalyze the oxidation of an optically active aldehyde to an optically active carboxylic acid. Such basicity can result from the catalyst functioning as a Lewis base or a Bronsted-Lowry base. The catalysts should be basic enough to promote decomposition of any aldehyde-peracid adduct but relatively unreactive with regard to oxidation by peracid. The basicity of the catalysts should also be sufficient to favor the oxidation reaction to optically active carboxylic acids over any competing aldehyde racemization reactions.

In an embodiment of this invention, if the amine and/or amine N-oxide catalyst has excessive basicity causing optically active aldehyde racemization, the optically active aldehyde racemization can be suppressed by adding a weak organic acid to the reaction mixture. Various weak organic acids, e.g., aliphatic and aromatic carboxylic acids, may be employed in the process of this invention. The weak organic acids should be sufficient to moderate basicity of the catalyst to suppress racemization. Preferred weak organic acids have a pKa 3–6 and include, for example, acetic acid. The weak organic acid is employed in an amount sufficient to moderate basicity of the catalyst to suppress racemization, preferably 1 equivalent with respect to the catalyst.

The amine and/or amine N-oxide catalyst is employed in a catalytically effective amount, i.e., an amount sufficient to catalyze the oxidation reaction. Preferably, the amine and/or amine N-oxide stoichiometry can range from about 0.1 to about 10 molar equivalents with respect to optically active aldehyde, preferably from about 0.5 to about 2 molar equivalents with respect to optically active aldehyde, and most preferably from about 0.7 to about 1.2 molar equivalents with respect to optically active aldehyde. The amine and/or amine N-oxide stoichiometry can affect the amount of formate byproduct formed in the process of this invention.

The catalysts used in the oxidation step of the process of this invention may optionally be supported. Advantages of a supported catalyst may include ease of catalyst separation. Illustrative examples of supports include alumina, silica gel, ion-exchange resins, polymeric supports and the like.

The process conditions employable in the oxidation step of the process of this invention are chosen to minimize aldehyde racemization and reduce formate byproducts.

The mode of addition of reaction ingredients in the oxidation step of the process of this invention is not narrowly critical. The mode of addition should be such that an optically active carboxylic acid is obtained. As an illustration, if the peracid is added to a mixture of optically active aldehyde and amine and/or amine N-oxide catalyst, the oxidation must be carried out before base-catalyzed racemization occurs.

The oxidation step of the process of this invention may be conducted at a reaction temperature from about −25° C. or lower to about 60° C. Lower reaction temperatures may generally tend to minimize formate byproduct formation. To minimize aldehyde racemization, the temperature should not exceed about 10° C. during exothermic peracid addition when using amines as catalysts. When using amine N-oxides as catalysts, temperatures should not exceed about 25° C. to minimize methyl ketone formation when oxidizing alpha-methyl substituted benzylic aldehydes. In general, oxidations at reaction temperatures of about −10° C. to about 25° C. are preferred.

The oxidation step of the process of this invention is conducted for a period of time sufficient to produce an enantiomerically enriched carboxylic acid mixture. The exact reaction time employed is dependent, in part, upon factors such as temperature, nature and proportion of starting materials, and the like. The reaction time will normally be within the range of from about one-half to about 200 hours or more, and preferably from less than about one to about 10 hours.

The oxidation step in the process of this invention can be carried out in the liquid state and can involve a batch or continuous liquid recycle system. A batch system is preferred for conducting such processes. Preferably, such oxidation involves a batch homogeneous catalysis process wherein the oxidation is carried out in the presence of any suitable conventional solvent as further described herein.

The oxidation step of the process of this invention may be conducted in the presence of an organic solvent. Depending on the particular catalyst and reactants employed, suitable organic solvents include, for example, alcohols, alkanes, ethers, aldehydes, esters, acids, amides, amines, aromatics and the like. Any suitable solvent which does not unduly adversely interfere with the intended oxidation process can be employed and such solvents may include those heretofore commonly employed in known processes. Mixtures of one or more different solvents may be employed if desired. Solvents which partially or totally dissolve the aldehyde and do not react with peracids may be useful. Organic esters are preferred solvents. Water and water/ethanol mixtures may also be useful solvents. The amount of solvent employed is not critical to this invention and need only be that amount sufficient to provide the reaction medium with the particular substrate and product concentration desired for a given process. In general, the amount of solvent when employed may range from about 5 percent by weight up to about 95 percent by weight or more based on the total weight of the reaction medium.

As indicated above, the carboxylic acid-forming process of this invention can be conducted in a batch or continuous fashion, with recycle of unconsumed starting materials if required. The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the amine and/or amine N-oxide catalyst. The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The carboxylic acid-forming process of this invention is useful for preparing mixtures of substituted optically active carboxylic acids. Illustrative optically active carboxylic acids prepared by the process of this invention include, for example, substituted carboxylic acids. Illustrative preferred optically active carboxylic acid compounds prepared by the oxidation process of this invention include, for example, S-2-(p-isobutylphenyl)propionic acid, S-2-(6-methoxy-2-naphthyl)propionic acid, S-2-(3-benzoylphenyl)-propionic acid, S-2-(p-thienoylphenyl)propionic acid, S-2-(3-fluoro-4- phenyl)phenylpropionic acid, S-2-[4-(1,3-dihydro-1-oxo-2H-isoindol-2-yl)phenyl]propionic acid and the like. Illustrative of suitable optically active carboxylic acids which can be prepared by the processes of this invention include those permissible optically active carboxylic acids which are described in Kirk-Othmer, Encyclopedia of Chemical Technology, Third Edition, 1984, the pertinent portions of which are incorporated herein by reference, and The Merck Index, An Encyclopedia of Chemicals, Drugs and Biologicals, Eleventh Edition, 1989, the pertinent portions of which are incorporated herein by reference.

The carboxylic acid-forming process of this invention can provide optically active carboxylic acids having very high enantioselectivity and regioselectivity. Enantiomeric excesses of preferably greater than 50%, more preferably greater than 85% and most preferably greater than 95% can be obtained by such processes. A number of important pharmaceutical compounds can be prepared by such oxidation processes including, but not limited to, S-naproxen, S-ibuprofen, S-ketoprofen, S-suprofen, S-flurbiprofen, S-indoprofen, S-tiaprofenic add and the like.

Illustrative of carboxylic acid-forming reactions and permissible derivatization reactions include, for example, reactions that involve the following reactant/aldehyde intermediate/product combinations:

| Reactant | Aldehyde Intermediate | Product |
|---|---|---|
| 2-vinyl-6-methoxy-naphthalene | S-2-(6-methoxy-2-naphthyl)-propionaldehyde | S-naproxen |
| 2-vinyl-6-methoxy-naphthalene | S-2-(6-methoxy-2-naphthyl)-propionaldehyde | S-naproxen sodium |
| p-isobutylstyrene | S-2-(p-isobutylphenyl)-propionaldehyde | S-ibuprofen |
| p-isobutylstyrene | S-2-(p-isobutylphenyl)-propionaldehyde | S-ibuprofen-L-lysinate |
| 4-ethenylphenyl-2-thienylketone | S-2-(p-thienoylphenyl)-propionaldehyde | S-suprofen |
| 4-ethenyl-2-fluoro-biphenyl | S-2-(3-fluoro-4-phenyl)-phenylpropionaldehyde | S-flurbiprofen |
| 4-(1,3-dihydro-1-oxo-2H-isoindol-2-yl)-styrene | S-2-[4-(1,3-dihydro-1-oxo-2H-isoindol-2-yl)-phenyl]propionaldehyde | S-indoprofen |
| 2-ethenyl-5-benzoylthiophene | S-2-(5-benzoyl-2 thienyl)-propionaldehyde | S-tiaprofenic acid |
| 3-ethenylphenyl phenyl ether | S-2-(3-phenoxy)propion-aldehyde | S-fenoprofen |
| propenylbenzene | S-2-phenylbutyraldehyde | S-phenetamid, S-butetamate pheneticillin |
| phenyl vinyl ether | S-2-phenoxypropional-dehyde | |
| vinyl chloride | S-2-chloropropional-dehyde | S-2-chloro-propionic acid |
| 5-(4-hydroxy)benzoyl-3H-pyrrolizine | 5-(4-hydroxy)benzoyl-1-formyl-2,3-dihydro-pyrrolizine | ketorolac or derivative |
| 3-ethenylphenyl phenyl ketone | R-2-(3-benzoylphenyl)-propionaldehyde | R-ketoprofen |
| 4-ethenyl-2-fluoro-biphenyl | R-2-(3-fluoro-4-phenyl)-phenylpropionaldehyde | R-flurbiprofen |

The optically active derivatives of the products of the process of this invention have a wide range of utility that is well known and documented in the prior art, e.g. they are especially useful as pharmaceuticals, flavors, fragrances, agricultural chemicals and the like. Illustrative therapeutic applications, include, for example, non-steroidal anti-inflammatory drugs, ACE inhibitors, beta-blockers, analgesics, bronchodilators, spasmolytics, antihistimines, antibiotics, antitumor agents and the like.

As used herein, the following terms have the indicated meanings:

Chiral—compounds which have a non-superimposable mirror image.

Achiral—compounds which do not have a non-superimposable mirror image.

Prochiral—compounds which have the potential to be converted to a chiral compound in a particular process.

Chiral center—any structural feature of a compound that is a site of asymmetry.

Racemic—a 50/50 mixture of two enantiomers of a chiral compound.

Stereoisomers—compounds which have identical chemical constitution, but differ as regards the arrangement of the atoms or groups in space.

Enantiomers—stereoisomers which are non-superimposable mirror images of one another.

Stereoselective—a process which produces a particular stereoisomer in favor of others.

Enantiomeric excess (ee)—a measure of the relative amounts of two enantiomers present in a product. ee may be calculated by the formula [amount of major enantiomer−amount of minor enantiomer]/[amount of major enantiomer+amount of minor enantiomer] and converted to percent.

Optical activity—an indirect measurement of the relative amounts of stereoisomers present in a given product. Chiral compounds have the ability to rotate plane polarized light. When one enantiomer is present in excess over the other, the mixture is optically active.

Optically active mixture—a mixture of stereoisomers which rotates plane polarized light due to an excess of one of the stereoisomers over the others.

Optically pure compound—a single enantiomer which rotates plane polarized light.

Regioisomers—compounds which have the same molecular formula but differing in the connectivity of the atoms.

Regioselective—a process which favors the production of a particular regioisomer over all others.

IsoBHA chloridite—1,1'-biphenyl-3,3'-di-t-butyl-5,5'-dimethoxy-2,2'-diylchlorophosphite.

(IsoBHA-P)$_2$2K4R-pentanediol—A ligand having the formula:

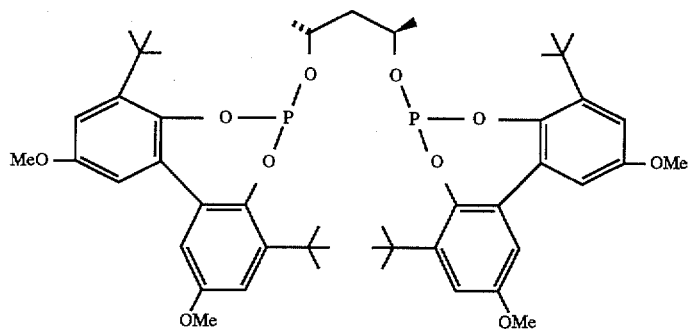

The latter ligand can be produced from Iso BHA chloridite by the process described in Example 1 of abovementioned PCT Patent Application 93/03839. The complete chemical name of this ligand is (2R, 4R)-Di[2,2'-(3,3'-di-tert-butyl-5,5'-dimethoxy-1,1'-biphenyl)]-2,4-pentyl diphosphite.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all compounds having at least one hydrogen and one carbon atom. In a broad aspect, the hydrocarbons include acyclic and cyclic, branched and unbranched, carbocyclic and heterocyclic, aromatic and nonaromatic organic compounds which can be substituted or unsubstituted.

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

As used herein, the following symbols have the indicated meanings:

| | |
|---|---|
| L | liter |
| mL | milliliter |
| wt % | weight percent |
| mL/min | milliliters per minute |
| ppm | parts per million by weight |
| g | grams |
| mg | milligrams |
| psi | pounds per square inch |
| °C. | degrees centigrade |
| b/n | branched to normal isomer ratio |
| cc | cubic centimeter |
| DSC | Differential Scanning Calorimeter |
| GC | Gas Chromatography |
| HPLC | High Performance Liquid Chromatography |
| mm | millimeter |
| mmol | millimoles |
| TLC | Thin Layer Chromatography |

The following Examples are provided to illustrate the process of this invention.

EXAMPLE 1

Improving Enantiomeric Purity of an Aldehyde Through Crystallization in Acetone

A solution consisting of 6-methoxy-2-vinylnaphthalene (395 g), Iso(BHA-P)$_2$-2R,4R-pentanediol (6.041 g), Rh$_4$(CO)$_{12}$ 0.862 g) and acetone (1500 mL) was charged to a 1 gallon reactor which was pressurized to 250 psi with 1:1 H$_2$/CO. The reaction mixture was stirred at ambient temperature for four days to effect hydroformylation. The crude reaction product so produced was removed from the reactor and an aliquot removed to determine the composition of the product.

GC analysis of the aliquot of the crude reaction product indicated that 98.8% of the olefin starting material had been converted to aldehydes and that a 95:1 ratio of 2-(6-methoxy-2-naphthyl)propionaldehyde to 3-(6-methoxy-2-naphthyl)-propionaldehyde had been obtained. Oxidation of the aldehydes in the aliquot followed by chiral High Performance Liquid Chromatography (HPLC) analysis of the resulting carboxylic acids indicated that an 81% ee of the desired S-aldehyde [i.e., S-2-(6-methoxy-2-naphthyl)-propionaldehyde] was produced.

The above-mentioned oxidation and HPLC analysis were conducted as follows: 3 mL of the crude reaction product was diluted in 50 mL of acetone and mixed with 0.3 g of potassium permanganate and 0.32 g of magnesium sulfate. The mixture so formed was stirred at room temperature for 30 minutes to effect oxidation of the aldehydes in the crude reaction product to the corresponding carboxylic acids. Then the acetone was removed under reduced pressure. The residue so produced was extracted three times with 50 mL of hot water and the three aqueous solutions so obtained were combined, filtered and washed with 50 mL of chloroform. The aqueous layer was then acidified with HCl to a pH of 2 at which time a white, solid precipitate formed. The precipitate was filtered, washed with water and dried to isolate the carboxylic acids. The carboxylic acids were analyzed by chiral HPLC on a CHIRACEL™ OD-H column which could separate the two enantiomers of the resulting 2-(6-methoxy-2-naphthyl)propionic acid.

The remainder of the crude reaction product was stored at −22° C. overnight and during that time crystals formed. These crystals were filtered, washed with cold acetone and dried under vacuum to yield 111 g of off-white crystals and a first filtrate. Analysis of the crystals indicated that the b/n isomer ratio had been increased to >250:1. Oxidation of the aldehydes to carboxylic acids and chiral HPLC of the resulting carboxylic acids indicated a 93% ee of the S-enantiomer had been obtained.

The first filtrate was stored overnight at −22° C. and additional crystals formed. These crystals were filtered, washed with cold acetone and dried under vacuum to yield a second filtrate and 70 g of white crystals with an b/n isomer ratio of 250:1 and a 93% ee of the S-enantiomer.

The second filtrate was stored at −22° C. overnight and again crystals formed. Filtration, washing and vacuum drying of these crystals resulted in isolation of 50 g of a crystalline aldehyde product having an b/n isomer ratio of 200:1 and an ee of 92% S-enantiomer.

EXAMPLE 2

Improving Enantiomeric Purity of Aldehydes Through Crystallization in Ethyl Acetate A solution consisting of 6-methoxy-2-vinylnaphthalene (60 g), Iso(BHA-P)$_2$-2R,4R-pentanediol (1.25 g), Rh$_4$(CO)$_{12}$ (0.131 g) and ethyl acetate (180 g) was charged to a 300 mL reactor which was pressurized to 250 psi with 1:1 H$_2$/CO. The reaction mixture so formed was stirred at ambient temperature for four days to effect hydroformylation. The crude reaction product was removed from the reactor and an aliquot removed to determine the composition of the product.

GC analysis of the aliquot indicated that 99% of the olefin starting material had been converted to aldehydes and that a 59:1 ratio of 2-(6-methoxy-2-naphthyl)propionaldehyde to 3-(6-methoxy-2-naphthyl)propionaldehyde had been obtained. Oxidation of the aldehyde products followed by chiral HPLC analysis of the resulting carboxylic acids indicated that an 80% ee of the desired S-aldehyde [i.e., S-2-(6-methoxy-2-naphthyl)propionaldehyde] was produced.

The remainder of the crude reaction product was then stored at −22° C. overnight, during which time crystals formed in the container. These crystals were filtered, washed with cold acetone and dried under vacuum to yield 32 g of off white crystals. Subsequent analysis of these crystals indicated that the b/n isomer ratio had been increased to >129:1. Oxidation of the crystalline aldehyde and chiral HPLC of the resulting carboxylic acid indicated a 92% ee of the S-enantiomer had been obtained.

EXAMPLE 3

Membrane Separation of An Aldehyde from Acetone Solution

A. A crude hydroformylation reaction product similar to the crude reaction product produced in Example 1 above was processed through a membrane to remove the rhodium and ligand. The crude reaction product contained 2-(6-methoxy-2-naphthyl)propionaldehyde (30 wt %) dissolved in acetone (70 wt %). The crude reaction product also contained rhodium (263.3 ppm) and ligand.

The membrane was arranged and used as follows: Three 2 inch circles were cut from an 8 inch×11 inch sheet of MPF-50 membranes (Lot #021192, code 5107) which are sold by Membrane Products Kiryat Weizmarm Ltd. and which are believed to be within the scope of abovementioned European Patent Application 0 532,199 A1. These circles were placed into three Osmonics membrane holders. The crude reaction product (feed) was placed into a 2 L Hoke cylinder under nitrogen. The feed was pumped to 500 psi at a flow rate of about 380 mL/min. The feed flowed through a 60 micron filter and then was split into three streams which went to the membranes. Flowmeters were used to ensure that the flow was split equally to the holders. The permeate from the membranes was combined and collected under nitrogen. The raffinate flowed to a back pressure regulator and was then returned to the Hoke cylinder.

About 1500 g of the crude reaction product was permeated and the rhodium content of the resulting first permeate was about 69.4 ppm. The membrane and equipment were washed with acetone and the acetone was discarded.

The above-described membrane separation was repeated on the 1500 g of the first permeate (which contained 69.4 ppm rhodium) and 1000 g of a solution (containing 19.2 ppm rhodium) was separated as a second permeate. The composition of the second permeate was 80% acetone and 20% solids. The b/n isomer ratio of the solids was 64:1 and it contained 1.4% normal isomer, 9.9% R-isomer, and 88.7% S-isomer [i.e., S-2-(6-methoxy-2-naphthyl)-propionaldehyde]. The enantiomeric excess (ee) of the crystalline solids was 80.7%. The second permeate so obtained was then concentrated and crystallized as described below.

A portion of the second permeate produced as described above was concentrated by evaporating acetone at 18° C. and 25 inches of mercury pressure to produce a concentrated solution containing 70% acetone and 30% solids. The concentrate so obtained was charged into a crystallizer described below. The crystallizer consisted of a jacketed, 250 cc vertical cylinder (A) fitted with a stirrer (B) and an internal filter (C). Crystallization was initiated by cooling the jacket to −14° C. thus cooling the contents of the cylinder to near −14° C. In order to dissolve the small crystals that formed on the inner surface of the cylinder and to enhance crystal size, the crystallizer was reheated to 3° C. and again cooled to −14° C. using cooler (D). This procedure was repeated three times. Since the internal filter (C) clogged, the solid crystals formed in the cylinder and liquid were removed from the crystallizer and separated in a laboratory vacuum filter. The resulting filter cake was washed with one part by weight of cold acetone (0° C.) per two parts (by weight) of wet solids (filter cake). The resultant crystalline filter cake contained 13% acetone and 87% crystalline solids and had a b/n isomer ratio of 386:1. The solids contained 0.3 normal isomer, 2.4% R-isomer and 97.3% S-isomer. The enantiomeric excess of the solids was 95.2%. Scanning Electron Microscope (SEM) photos indicated that solid particles were uniform and about 100 microns in size.

B. The concentration and crystallization procedure of A above was repeated with another portion of the second permeate obtained in the above-described membrane separation and the crystals produced had a b/n isomer ratio of 446:1 and contained of 0.2% normal isomer, 2.7% R-isomer, and 97.1% S-isomer. The ee of the crystals was 94.6%.

C. The wet filter cakes produced via the procedures of A and B above were combined and dissolved in two parts by weight of acetone per part by weight of the combined wet filter cake. The solution so obtained was crystallized using the crystallization procedure of A above, separated and washed per the procedure of A above. The resultant crystals had a b/n isomer ratio of 921:1 and contained 0.1 normal isomer, 1.3% R-isomer, and 98.6% S-isomer. The ee of the crystals was 97.4%.

D. The wet crystalline filter cake produced by procedure of C above was dissolved in two parts (by weight) of acetone per part of the combined wet cake and crystallized using the crystallization procedure of A above, separated and washed according to the procedure of A above. The final crystals so obtained had a b/n isomer ratio of 1836:1. The crystal contained 0.05% normal isomer, 0.6% R-isomer, 99.35% S-isomer and 4 ppm rhodium. The ee of the crystals was 98.8%. The melting point of the crystals was 72.5° C. determined in a Differential Scanning Calorimeter (DSC).

EXAMPLE 4

Refining An Aldehyde from Ethyl Acetate Solution

A. A crude hydroformylation reaction product was used that was similar to the crude reaction product produced in Example 2 above and that was composed of 62.9% ethyl acetate and 37.1% solids containing 2-(6-methoxy-2-naphthyl)propionaldehyde. The solids had a b/n of 42:1 were composed of 2.3% normal isomer, 11.7% R-isomer and 86% S-isomer [i.e., S-2-(6-methoxy-2-naphthyl)-propionaldehyde] and had an ee of 76%. The crude reaction product was crystallized as follows:

B. Seven successive 250 ml charges of the crude reaction product were cooled to −7° C. in the crystallizer used in Example 3 above. The crystals and liquid resulting from the crystallization were separated on an external vacuum filter and the crystals were washed with 0.5 parts of ethyl acetate per part of wet cake. The resultant composite cake from the seven crystallizations contained 24% ethyl acetate and 76% crystalline solids. The b/n isomer ratio of the crystalline solids was 123:1 and the solids contained 0.8% normal isomer, 6.0% R-isomer, and 93.2% S-isomer. The ee of the crystalline solids was 87.9%.

C. The wet filter cake from step B. above was dissolved in two parts by weight of ethyl acetate per part (by weight) of wet filter cake. The solution was cooled to −13° C. in the laboratory crystallizer used in Example 3 above. The contents of the crystallizer were then reheated to 3° C. and again cooled to −13° C. This cool-reheat cycle was repeated two times to enhance the crystal size. The solid-liquid mixture so produced was separated in an external vacuum filter and the wet filter cake 50 produced was washed with 0.5 parts of cold (−10° C.) ethyl acetate per part of wet filter cake. The resultant cake contained 25% ethyl acetate and 75% crystalline solids. The crystalline solids had a b/n isomer ratio of 483:1 and had, a normal isomer content of 2%, a R-isomer content of 1.6% and a S-isomer content of 98.2%. The ee of the crystalline solids was 96.8%.

EXAMPLE 5

Refining of An Aldehyde from Acetone Solution in a Falling Film Crystallizer

Crude hydroformylation reaction product that was similar to the crude reaction product produced in Example 1 above and that contained 70% acetone and 30% solids was refined in a laboratory falling film Crystallizer. The solids in the crude reaction product had a b/n isomer ratio of 69:1 and the solids composition was 1.4% normal isomer, 8.9% R-isomer, and 89.7% S-isomer [i.e., S-2-(6-methoxy-2-naphthyl)propionaldehyde]. The enantiomeric excess of the solids was 81.9%.

The crude reaction product was concentrated by evaporating 30% by weight of the solution. The resulting concentrate consisted of 57% acetone and 43% solids. This was crystallized in a laboratory falling film crystallizer by the following procedure.

The crystallizer consisted of a kettle (A), a jacketed column (B) {the column was a one meter long jacketed vertical tube having a one inch diameter internal opening} and (D) means for pumping (i.e., circulating) liquid from the kettle to the film device (C) at the top of the falling film crystallizer. The jacket of the crystallizer was affixed to a supply of coolant (E) which flowed co-current with the falling film. That is, both the falling film and the coolant in the jacket flowed downward in a co-current fashion. The crystallizer used is similar in principle of operation to those described in above-mentioned U.S. Pat. No. 3,621,664.

Two thousand milliliters of the concentrate produced as described above were charged to the kettle (A) of the falling film crystallizer used in this Example 5. The concentrate in the kettle was circulated briefly down through the column (B) to wet the inside walls and then circulation was discontinued. Since the walls of the column were maintained at −20° C. by circulating coolant, a thin frosting of solids quickly formed on the inner walls of the column. The flow through the falling film crystallizer was resumed depositing crystals on the inside of column wall. After the kettle temperature was reduced to −16° C., the recirculation flow was stopped. During the cooling, a slight amount of heat was added to the kettle by a heating mantle (F) to prevent crystallization in the kettle. To compensate for this heating, the recirculating liquid was cooled slightly by circulating coolant from bath (G) to coolers (H). After crystallization was complete, the residual liquid in the kettle was emptied and the solids inside the crystallizer walls were washed with 50 cc of wash liquid that was added from the top of the column and this wash liquid was discarded. The composition of the kettle residue was 61% acetone and 39% solids. The solids in the kettle had a b/n isomer ratio of 60:1 and contained 1.6% normal isomer, 12.8% R-isomer and 85.6% S-isomer. The ee of the kettle solids was 74.0%.

600 cc of reagant grade acetone was added to the kettle and circulated to the falling film device at 20° C. and then down the inside wall of the column to dissolve the solids adhering to the inside of the column. This was a very quick and efficient technique for recovering adhering solids and is a unique method for recovery of solids from the falling film crystallizer.

The acetone solution recovered from the column wall contained 78% acetone and 22% crystalline solids. The crystalline solids had a b/n isomer ratio of 111:1 and contained 0.9% normal isomer, 6.9% R-isomer and 92.2% S-isomer. The crystalline solids ee was 86.1%.

EXAMPLE 6

Refining of An Aldehyde from Acetone Solution Utilizing Cooling Crystallization

Three 2 inch circles from an 8.5 inch×11 inch sheet of MPF-50 membranes (LOT #021192 code 5102). These were placed into three Osmonics membrane holders. Feed was placed into a 2 L Hoke cylinder under nitrogen. The feed was pumped to 500 psi at a flow rate of about 380 mL/min. The feed flowed through a 60 micron filter and then was split into three streams which went to the membranes. Flowmeters were used to ensure that the flow was split equally. The permeate from the membranes was combined and collected under nitrogen. The raffinate flowed to a back pressure regulator and then was returned to the Hoke cylinder.

The feed was a 4 L batch of a crude hydroformylation reaction product containing 2-(6-methoxy-2-naphthyl)-propionaldehydes (30 wt %) in acetone (70 wt %). The mixture also contained rhodium (389.3 ppm) and Iso(BHA-P)2-2R,4R-pentanediol. About 3325 g of this solution was permeated through the membrane and the resulting permeate solution had a rhodium content about 36.3 ppm. The system was emptied, cleaned with acetone and the waste discarded.

The 3325 g of the permeate solution containing 36.3 ppm rhodium was placed back into the Hoke cylinder and about 1439 g of this solution was again permeated through the membrane. The resulting permeate solution contained about 5.6 ppm rhodium.

The 1439 g of the solution containing 5.6 ppm rhodium was placed back into the Hoke cylinder and passed back through the membrane for the third time. About 935 g of this solution was permeated through the membrane and the resulting permeate had about 1.2 ppm rhodium. This permeate was then used as a feed for the crystallization process described below.

Recovery and refining of S-2-(6-methoxy-2-naphthyl)-propionaldehyde aldehyde from the permeate obtained as described above was accomplished by the sequence of operations described below. In summary, the permeate feed solution was batch crystallized by cooling to −10° C. The slurry so obtained was filtered to remove crystals and the crystals were washed with one half gram of acetone per gram of wet solids. The filtrate and was were combined and the solution concentrated to 40 percent solids by evaporating acetone. The crystallization, filtration and washing was repeated on this concentrated solution. The crystals from this second stage were combined with crystals from the first crystallization and dissolved in one and one half parts by weight of acetone per part of wet solids. This solution was processed in the same manner as the original permeate feed solution. The solids that were recovered and washed from both crystallization stages were again combined and dissolved in acetone. The final recrystallization was also conducted in the manner as described above in this Example. The refined crystalline solids from this last stage represented the final product (i.e., S-2-(6-methoxy-2-naphthyl)propionaldehyde). The final ee was 96.8. The yield of S-2-(6-methoxy-2-naphthyl)propionaldehyde as a fraction of that supplied in the feed was 26.8 percent.

EXAMPLE 7

A. Naproxen Aldehyde Melting Point Diagram

Experimental melting point data was obtained using the crystallizer described in Example 3 above. Samples were obtained during crystallization tests in acetone solutions. The solid samples were removed from the slurry by filtration. The samples were then slowly heated in a Perkin/Elmer DSC7 to obtain the melting point. The data are tabulated in Table 1.

The melting point of pure S enantiomer (S-2-(6-methoxy-2-naphthyl)propionaldehyde) is discernible. It is difficult to develop a complete liquidus curve for a variety of reasons. A problem with melting point determination of such solid samples is that N isomer is present in sufficient concentration to depress the mixture melting point.

TABLE 1

Naproxen Aldehyde Melting Point Data

| Sample Composition | | | |
|---|---|---|---|
| % S | % R | % N | Melting Point, °C. |
| 98.2 | 1.7 | 0.1 | 73.5 |
| 94.3 | 5.0 | 0.7 | 66.1 |
| 98.2 | 1.6 | 0.2 | 72.7 |
| 94.8 | 4.7 | 0.5 | 69.4 |
| 87.4 | 10.8 | 1.8 | 63.7 |
| 95.5 | 4.0 | 0.5 | 72.5 |
| 88.1 | 8.7 | 3.2 | 57.2 |
| 92.3 | 7.0 | 0.7 | 66.9 |

B. Naproxen Aldehyde Solubility

Solubility data for solids in acetone solvent were obtained by visually obtaining a "cloud" point for a solution of known composition by slowly cooling the solution. After obtaining a "cloud" point the solution was slowly heated until a "clear" point was observed. The "clear" point represents the saturation temperature of the solution and the "cloud" point the temperature at which massive spontaneous nucleation occurs. The data are shown in Table 2.

Naproxen aldehydes [i.e., R- and S-2-(6-methoxy-2-naphthyl)propionaldehyde] are very soluble in acetone. The solubility of these aldehydes is very sensitive to temperature and a high degree of solution subcooling is required to nucleate the solution.

TABLE 2

Naproxen Aldehyde Solubility Data in Acetone

| Solids (wt %) | Ratio Solids/Liquid | Clear Point, °C. | Cloud Point, °C. |
|---|---|---|---|
| 29.0 | 0.41 | 6 | −17 |
| 35.3 | 0.55 | 15 | −9 |
| 30.0 | 0.43 | 11 | −6 |
| 22.0 | 0.28 | 1 | −15 |
| 47.0 | 0.89 | 25 | 5 |

EXAMPLE 8

Recovery of S-Naproxen Aldehyde from Acetone Solution

A crude reaction product of an asymmetric hydroformylation reaction was produced with low ee (62%) to experimentally investigate the quality of S-naproxen aldehyde [i.e., S-2-(6-methoxy-2-naphthyl)propionaldehyde] that can be recovered from solutions with high concentrations of corresponding isomeric R- and N-aldehydes. Using the cooling crystallization procedure described in Example 3 above (i.e., the solution is cooled to −15° C., reheated to 0° C. and this technique repeated three times before a final cool down to minus 15), a feed solution containing 77.6% S-isomer, 18.2% R-isomer and 4.2% N-isomer and having an enantiomeric excess (ee) of 62% was processed. The resulting crystals were recovered on a vacuum filter and washed with cold acetone. The composition of the crystals was 95.5% S-isomer, 4.0% R-isomer, and 0.5% N-isomer giving an enantiomeric excess of 92%. The filtrate recovered from the crystallization procedure described above in this Example and having a solids concentration of 65.5% S-isomer, 26.8% R-isomer and 7.7% N-isomer was concentrated to 53% solids by evaporating acetone under vacuum. The concentrate so obtained was crystallized using the crystallization procedure described above in this Example. The composition of the crystalline solids obtained by the latter crystallization was 92.3% S-isomer, 7.0% R-isomer and 0.7% N-isomer. The enantiomeric excess of those solids was 85.9%. The composition of the solids in the final tiltrate was 54.1% S-isomer, 37.6% R-isomer and 8.3% N-isomer.

EXAMPLE 9

Improving Enantiomeric Purity of 2-(p-Isobutylphenyl)propionaldehyde Through Melt Crystallization A solution was prepared consisting of p-isobutylstyrene (100.2 g), Iso(BHA-P)$_2$-2R,4R-pentanediol (0.85 g), and Rh$_4$(CO)$_{12}$ (0.091 g). 100 mL of the mixture so formed was charged to a 300 mL reactor which was pressurized with 1:1 H$_2$/CO. The mixture was stirred at 25° C. for 46 hours at 130 psi to effect hydroformylation. The crude reaction product was removed from the reactor and an aliquot removed to determine the composition of the product.

GC analysis on a beta-cyclodextrin chiral capillary column (Cyclodex-B™) indicated that 99.4% of the olefin starting material had been converted to aldehydes and that a 42:1 ratio of 2-(p-isobutylphenyl)propionaldehyde to 3-(p-isobutylphenyl)propionaldehyde had been obtained. Oxidation of the aldehyde products followed by chiral gas chromatography of the resulting carboxylic acids indicated that an 85±5% ee of the desired S-aldehyde [i.e., S-2-(p-isobutylphenyl)propionaldehyde] was produced.

A portion (25 mL, 23.54 g) of the crude product was flash distilled to separate the products from the catalyst. The first cut (12.4 g) was obtained at 89°–92° C. head temperature at a pressure of 1 mm of Hg. A second cut (9.4 g) was obtained at 83°–4° C. at 0.6 mm of Hg, and a small amount was left as residue. The second cut was partially frozen and some liquid (3.27 g) was withdrawn, first with a pipet and then a flitted glass filter stick with the liquid at −12° to −17° C.

Oxidation of portions of the liquid and crystals with sodium chlorite followed by chiral gas chromatography of the resulting carboxylic acids indicated 92±1 and 75±2% ee for the S-aldehyde in the crystals and and liquid respectively. The ratios of the concentrations of other impurities in liquid to their concentrations in the crystals averaged 2.2 and the b/n ratio in the crystals was 54:1.

The oxidation with sodium chlorite referred to above was conducted as follows:

A mixture of 0.28 gram of aldehyde and 2.0 mL of distilled water was cooled to 0° C. and stirred. Aqueous sodium sulfamate (3 mL of 1M, adjusted to pH 5 with phosphoric acid) and sodium chlorite (0.61 mL of 20%) solutions were added. After 15 minutes, the cooling bath was removed and the solution was stirred for an additional 15 minutes as it was allowed to warm to room temperature. The pH was adjusted to 9.5 with 0.5 mL of 1N sodium hydroxide and the material rinsed with water into a separatory funnel. The solution was shaken with added dichloromethane (10 mL) to extract neutral compounds. The aqueous layer was separated and acidified to pH<2 with concentrated hydrochloric acid. The cloudy mixture that formed was extracted with 20 mL of dichloromethane, toluene was added as an internal standard, and a small sample was taken to determine the yields of branched and normal acids by gas chromatography. The remaining solution was dried over anhydrous magnesium sulfate and filtered. The dichloromethane was removed with a rotary evaporator under vacuum (~150 mm Hg) with the bath at 60° C. The residue (0.02 g)was dissolved in toluene and analyzed by chiral gas chromatography.

EXAMPLE 10

Refining of An Aldehyde from Acetone Solution Utilizing Cooling Crystallization and Non-Solvent Addition Crude hydroformylation reaction product (47 g) that was similar to the crude reaction product produced in Example 1 above and that contained 70.5 g of acetone was partially refined in a laboratory crystallizer in a manner similar to Example 6. The solids in the partially refined reaction product had 97.65% S-isomer [i.e., S-2-(6-methoxy-2-naphthyl)propionaldehyde]. The partially refined product was further precipitated by adding non-solvent (water) at the final crystallizer condition. The quantity of water added was 0.5 cc per cc of crystallized slurry. The quality of the S-isomer recovered after vacuum filtration and washing with 150 cc of water was 97.87%. The quantity of material recovered was 40 g. By repeating this procedure four times, product quality increased to 99.10% ( 98.2% ee) with a recovery of 28 g.

EXAMPLE 11

Refining of An Aldehyde from Acetone Solution Utilizing Vacuum Cooling

Crude hydroformylation reaction product (666 g) that was similar to the crude reaction product produced in Example 1 above and that contained 40% acetone and 60% solids was added to a crystallization apparatus designed to provide vacuum cooling as described below. The solids had a b/n ratio (2-(6-methoxy-2-naphthyl)propionaldehyde to 3-(6-methoxy-2-naphthyl)-propionaldehyde) of 82.76:1 and a 76% ee of the S-isomer [i.e., S-2-(6-methoxy-2-naphthyl)propionaldehyde]. The apparatus consisted of a jacketed one liter kettle equipped with stirrer, condenser and vacuum pump. The solution was cooled to 5° C., where crystals formed, and then to 0° C. by slowly reducing the vacuum to a final reading of 50 mm absolute. The contents of the kettle were maintained at 0° C. for 15 minutes and then heated to 8° C. by increasing system pressure to 150 mm and warming the kettle jacket to 10° C. to heat the contents. Conditions in the kettle were maintained at 8° C. for 10 minutes, vacuum was again reduced to 50 mm and the kettle temperature reduced to 0° C. This heat back technique was employed to dissolve fine crystals and re-deposit the supersaturation onto existing crystals thereby enhancing the crystal size. After maintaining kettle temperature at 0° C. for 10 minutes the contents were separated in a laboratory centrifugal filter and washed with cold acetone. About 60 g of dry solids were recovered with a b/n ratio of 440:1 and an ee of 92.3%.

EXAMPLE 12

Oxidation Of (S)-2-(6-Methoxy-2-naphthyl) propionaldehyde To S-Naproxen Using Lutidine/ Acetic Acid As Catalyst To a stirred solution of 16.67 g (77.8 mmol) of (S)-2-(6-methoxy-2-naphthyl)propionaldehyde (naproxen aldehyde) in ethyl acetate (78 mL) cooled in a wet-ice bath (ca. 2° C.) was added concurrently 4.67 g (77.8 mmol) of glacial acetic acid and 8.33 g (77.8 mmol) of 2,6-dimethylpyridine (2,6-lutidine). To this solution was then added slowly dropwise 8.87 g (116.7 mmol) of a 23.7 weight percent solution of peracetic acid in ethyl acetate, at a rate slow enough such that the reaction temperature did not exceed 10° C. (ca. 1 hour). After the initial exotherm, the temperature returned to 2° C., and the reaction was maintained at this temperature for an additional 3.5 hours. Conversion of aldehyde at this time was ca. 99%, as monitored by GC (DB-1 column). The cold reaction solution was then transferred into a separatory funnel, was diluted with ethyl acetate (300 mL), and was washed with a 5% aqueous solution of sodium thiosulfate ($Na_2S_2O_3$, 100 mL). The ethyl acetate layer was further washed with two portions of water (110 mL each), and the combined water washes were back-extracted with ethyl acetate (100 mL). The combined ethyl acetate layers were extracted with two portions of a 5% aqueous solution of sodium hydroxide (NaOH, 110 mL each). The combined NaOH solutions of sodium naproxenate were acidified to pH=1 with a 10% aqueous solution of hydrochloric acid, precipitating the naproxen acid. The mixture was cooled in a wet-ice bath, and then was vacuum filtered through a #4 Whatman filter. The white solid thus obtained was dried in a vacuum oven overnight at 45° C. (25 mm Hg), giving 15.85 g (88.5%) of naproxen. HPLC analysis of this material (Chiracel OD-H column) indicated an 'S' acid content of 99.2%, the same as the starting aldehyde as measured following $KMnO_4$ oxidation.

EXAMPLE 13

Oxidation Of (S)-2-(4-Isobutylphenyl) propionaldehyde To (S)-Ibuprofen Using Lutidine/ Acetic Acid As Catalyst To a stirred solution of 109 g (573 mmol) of 2-(4-isobutylphenyl)-propionaldehyde (ibuprofen aldehyde) in ethyl acetate (5 12 mL) cooled in a wet-ice bath (ca. 2° C.) was added concurrently 34.4 g (573 mmol) of glacial acetic acid and 61.4 g (573 mmol) of 2,6-dimethyl pyridine (2,6-lutidine). To this solution was then added slowly dropwise 276 mL (859 mmol) of a 23.7 weight percent solution of peracetic acid in ethyl acetate, at a rate slow enough such that the reaction temperature did not exceed 7° C. (ca. 1 h 40 min). After the initial exotherm, the temperature returned to 2° C., and the reaction was maintained at this temperature for an additional 2 hours. Conversion of aldehyde at this time was ca. 99%, as monitored by GC (DB-1 column). The cold reaction solution was then transferred into a separatory funnel, was diluted with ethyl acetate (650 mL), and was washed with a 7% aqueous solution of sodium thiosulfate ($Na_2S_2O_3$, 500 mL). The ethyl acetate layer was further washed with two portions of water (750 mL each), and the combined water washes were back-extracted with ethyl acetate (300 mL). The combined ethyl acetate layers were extracted with three portions of a 5% aqueous solution of sodium hydroxide (NaOH, 750 mL twice, then 500 mL). The combined NaOH solutions were acidified to pH=1 with a 10% aqueous solution of hydrochloric acid. The resulting solution was extracted with three portions of dichloromethane (500 mL twice, then 300 mL), and the extract was dried over anhydrous $Na_2SO_4$. The extract was concentrated in vacuo to give 109 g (92.2%) of ibuprofen as an off-white solid. HPLC analysis of this material indicated an 'S' acid content of 83%, the same as the starting aldehyde as measured following $KMnO_4$ oxidation.

EXAMPLE 14

Oxidation Of (S)-2-(6-Methoxy-2-naphthyl) propionaldehyde To S-Naproxen Using Lutidine N-Oxide As Catalyst To a stirred solution of 3.32 g (15.5 mmol) of (S)-2-(6-methoxy-2-naphthyl)propionaldehyde (98.8% pure by GC) in n-butyl acetate (15.5 mL) cooled in a wet-ice bath (ca. 2° C.) was added 1.91 g (15.5 mmol) of 2,6-dimethylpyridine N-oxide (2,6-lutidine N-oxide). To this solution was then added slowly dropwise 1.77 g (23.2 mmol) of a 20.4 weight percent solution of peracetic acid in ethyl acetate, at a rate slow enough such that the reaction temperature did not exceed 10° C. (ca. 30 min). After the initial exotherm, the temperature returned to 2° C., and the reaction was maintained at this temperature for an additional 2 hours. Conversion of aldehyde at this time was ca. 99%, as monitored by GC (DB-1 column). The reaction solution was transferred into a separatory funnel, was diluted with n-butyl acetate (70 mL), and was washed with a 5% aqueous solution of sodium thiosulfate ($Na_2S_2O_3$, 15 mL). The butyl acetate layer was further washed with water (50 mL), and the combined water washes were back-extracted with n-butyl acetate (30 mL). The combined butyl acetate layers were extracted with two portions of a 5% aqueous solution of sodium hydroxide (NaOH, 65 mL each). The combined NaOH solutions of sodium naproxenate were acidified to pH=1 with a 5% aqueous solution of hydrochloric acid, precipitating the naproxen acid. The mixture was cooled in a wet-ice bath, and then was vacuum filtered through a #1 Whatman filter. The filter cake was washed with cold water (50 mL) and the white solid thus obtained was dried in a vacuum oven 60 hours at 55° C. (25 mm Hg), giving 3.51 g (98.4%) of naproxen.

EXAMPLE 15

Oxidation Of (S)-2-(6-Methoxy-2-naphthyl) propionaldehyde To S-Naproxen Using Pyridine N-Oxide/Acetic Acid As Catalyst To a stirred solution of 2.00 g (9.3 mmol) of (S)-2-(6-methoxy-2-naphthyl)propionaldehyde in ethyl acetate (10 mL) cooled in a wet-ice bath (ca. 2° C.) was added concurrently 0.89 g (9.3 mmol) of pyridine N-oxide and 0.56 g (9.3 mmol) of acetic acid. To this solution was then added slowly dropwise 5.8 mL (14.0 mmol) of a 20.4 weight percent solution of peracetic acid in ethyl acetate, at a rate slow enough such that the reaction temperature did not exceed 10° C. (ca. 15 minutes). After the initial exotherm, the temperature returned to 2° C., and the reaction was maintained at this temperature for an additional 4 hours. The reaction solution was transferred into a separatory funnel, was diluted with ethyl acetate (15 mL), and was washed with a 0.1N aqueous solution of sodium thiosulfate ($Na_2S_2O_3$, 25 mL). The ethyl acetate layer was further washed with water (10 mL), and the combined water washes were back-extracted with ethyl acetate (10 mL). The combined ethyl acetate layers were extracted with two portions of a 5% aqueous solution of potassium hydroxide (KOH, 65 mL then 25 mL). The combined KOH solutions of potassium naproxenate were acidified to pH=1 with a 5% aqueous solution of hydrochloric acid, precipitating the naproxen acid. The mixture was cooled in a wet-ice bath, and then was vacuum filtered through a #1 Whatman filter. The filter cake was washed with cold water (20 mL) and the white solid thus obtained was dried in a vacuum oven 18 hours at 55° C. (25 mm Hg), giving 1.72 g (80.0%) of naproxen.

EXAMPLE 16

Oxidation Of (S)-2-(4-Isobutylphenyl) propionaldehyde To (S)-Ibuprofen Using Lutidine N-Oxide As Catalyst To a stirred solution of 10.0 g (52.6 mmol) of 2-(4-isobutylphenyl)propionaldehyde (ibuprofen aldehyde)in n-butyl acetate (53 mL) cooled in a wet-ice bath (ca. 2° C.) was added 6.5 g (52.6 mmol) of 2,6-dimethylpyridine N-oxide (2,6-lutidine N-oxide). To this solution was then added slowly dropwise 29 mL (78.8 mmol) of a 20.0 weight percent solution of peracetic acid in ethyl acetate, at a rate slow enough such that the reaction temperature did not exceed 10° C. (ca. 25 minutes). After the initial exotherm, the temperature returned to 2° C., and the reaction was maintained at this temperature for an additional 4 hours. The cold reaction solution was then transferred into a separatory funnel, was diluted with n-butyl acetate (100 mL), and was washed with a 1% aqueous solution of sodium thiosulfate ($Na_2S_2O_3$, 100 mL). The butyl acetate layer was further washed with two portions of water (100 mL each), and the combined water washes were back-extracted with n-butyl acetate (100 mL). The combined butyl acetate layers were extracted with two portions of a 5% aqueous solution of sodium hydroxide (NaOH, 100 mL each). The combined NaOH solutions were acidified to pH=1 with a 10% aqueous solution of hydrochloric acid. The resulting solution was extracted with two portions of dichloromethane (100 mL each), and the extract was dried over anhydrous $Na_2SO_4$. The extract was filtered and concentrated in vacuo to give 10.3 g (94.6%) of ibuprofen as an off-white solid.

EXAMPLE 17

Oxidation Of (S)-2-(6-Methoxy-2-naphthyl) propionaldehyde To S-Naproxen With Peracetic Acid (1.5 Equivalents) Using 4-Methylmorpholine N-Oxide (1.0 Equivalent) As Catalyst To a stirred solution of 3.0 g (14.0 mmol) of (S)-2-(6-methoxy-2-naphthyl)propionaldehyde (ca. 95% pure by GC) in n-butyl acetate (14.0 mL) cooled in a wet-ice bath (ca. 2° C.) was added 1.64 g (14.0 mmol) of 4-methylmorpholine N-oxide. To this solution was then added slowly dropwise 7.7 mL (21.0 mmol) of a 23.0 weight percent solution of peracetic acid in ethyl acetate, at a rate slow enough such that the reaction temperature did not exceed 5° C. (highly exothermic, ca. 60 minutes). TLC analysis of the reaction mixture 10 minutes post peracetic acid addition indicated that conversion of the aldehyde was complete, and a sample (0.5 mL) was withdrawn for GC analysis. The reaction solution was transferred into a separatory funnel with the aid of n-butyl acetate (25 mL), and was washed with a 1M aqueous solution of sodium thiosulfate ($Na_2S_2O_3$, 5 mL). The butyl acetate layer was further washed with water (50 mL). The butyl acetate solution of naproxen acid was then extracted with two portions of a 5% aqueous solution of sodium hydroxide (NaOH, 50 mL each). The combined NaOH solutions of sodium naproxenate were acidified with stirring to pH=1 with a 5% aqueous solution of hydrochloric acid (105 mL), precipitating the naproxen acid. The mixture was vacuum filtered through a #1 Whatman filter, and the solids were washed with cold water (5 mL). The white solid thus obtained was dried in a vacuum oven 14 hours at 55° C. (25 mm Hg), giving 2.52 g (78.2%, not including withdrawn sample) of naproxen. Chiral phase HPLC analysis indicated a ratio of S: R naproxen of 50.1: 49.9 (racemic).

EXAMPLE 18

Oxidation Of (S)-2-(6-Methoxy-2-naphthyl) propionaldehyde To S-Naproxen With Peracetic Acid (1.5 Equivalents) Using 4-Methoxy-pyridine N-Oxide (1.0 Equivalent) As Catalyst To a stirred solution of 3.0 g (14.0 mmol) of (S)-2-(6-methoxy-2-naphthyl)propionaldehyde (ca. 95% pure by GC) in n-butyl acetate (14.0 mL) cooled in a wet-ice bath (ca. 2° C.) was added 1.75 g (14.0 mmol) of 4-methoxypyridine N-oxide. To this solution was then added slowly dropwise 7.7 mL (21.0 mmol) of a 23.0 weight percent solution of peracetic acid in ethyl acetate, at a rate slow enough such that the reaction temperature did not exceed 5° C. (highly exothermic, ca. 60 minutes). TLC analysis of the reaction mixture 10 minutes post peracetic acid addition indicated that conversion of the aldehyde was complete, and a sample (0.5 mL) was withdrawn for GC analysis. The reaction solution was transferred into a separatory funnel with the aid of n-butyl acetate (25 mL), and was washed with a 1M aqueous solution of sodium thiosulfate ($Na_2S_2O_3$, 5 mL). The butyl acetate layer was further washed with water (50 mL). The butyl acetate solution of naproxen acid was then extracted with two portions of a 5% aqueous solution of sodium hydroxide (NaOH, 50 mL each). The combined NaOH solutions of sodium naproxenate were acidified with stirring to pH=1 with a 5% aqueous solution of hydrochloric acid (105 mL), precipitating the naproxen acid. The mixture was vacuum filtered through a #1 Whatman filter, and the solids were washed with cold water (5 mL). The white solid thus obtained was dried in a vacuum oven 14 hours at 55° C. (25 mm Hg), giving 2.75 g (85.4%, not including withdrawn sample) of naproxen. Chiral phase HPLC analysis indicated a ratio of S:R naproxen of 88.5:11.4 (77.1%ee), the same ratio as the starting aldehyde within experimental error.

EXAMPLE 19

Oxidation Of (S)-2-(6-Methoxy-2-naphthyl) propionaldehyde To S-Naproxen With Peracetic Acid (1.1 Equivalents) Using 4-Methoxy-pyridine N-Oxide (0.5 Equivalents) As Catalyst At 2°-5° C.

To a stirred solution of 5.0 g (23.3 mmol) of (S)-2-(6-methoxy-2-naphthyl)propionaldehyde (ca. 95% pure by GC) in n-butyl acetate (24.0 mL) cooled in a wet-ice bath (ca. 2° C.) was added 1.46 g (11.67 mmol) of 4-methoxypyridine N-oxide. To this solution was then added slowly dropwise 1.95 g (25.67 mmol) of a 23.0 weight percent solution of peracetic acid in ethyl acetate, at a rate slow enough such that the reaction temperature did not exceed 5° C. (highly exothermic, ca. 45 min). TLC analysis of the reaction mixture 30 minutes post peracetic acid addition indicated that conversion of the aldehyde was complete. The reaction solution was transferred into a separatory funnel with the aid of n-butyl acetate (50 mL), and was treated with a 1M aqueous solution of sodium thiosulfate ($Na_2S_2O_3$, 1.3 mL). A sample (0.5 mL) was withdrawn for GC analysis. The butyl acetate layer was washed with water (50 mL, twice), and the washings were back-extracted with n-butyl acetate (20 mL). The combined butyl acetate solutions of naproxen acid were then extracted with two portions of a 5% aqueous solution of sodium hydroxide (NaOH, 60 mL each). The combined NaOH solutions of sodium naproxenate were acidified with stirring to pH=1 with a 5% aqueous solution of hydrochloric acid (125 mL), precipitating the naproxen acid. The mixture was cooled in a wet-ice bath, vacuum filtered through a #1 Whatman filter, and the solids were washed with cold water (5 mL). The white solid thus obtained was dried in a vacuum oven 14 hours at 55° C. (25 mm Hg), giving 4.91 g (91.4%, not including withdrawn sample) of naproxen. Chiral phase HPLC analysis indicated a ratio of S:R naproxen of 88.6: 11.4 (77.2 %ee), the same ratio as the starting aldehyde within experimental error.

EXAMPLE 20

Oxidation Of (S)-2-(6-Methoxy-2-naphthyl) propionaldehyde To S-Naproxen With Peracetic Acid (1.1 Equivalents) Using 4-Methoxy-pyridine N-Oxide (0.5 Equivalents) As Catalyst At −25° C.

To a stirred solution of 1.0 g (4.67 mmol) of (S)-2-(6-methoxy-2-naphthyl)propionaldehyde (ca. 95% pure by GC) in n-butyl acetate (5 mL) cooled in a $CO_2/CCl_4$ bath (−25° C.) was added 292 mg (2.3 mmol) of 4-methoxypyridine N-oxide. To this solution was then added slowly dropwise 391 mg (5.1 mmol) of a 23.0 weight percent solution of peracetic acid in ethyl acetate, at a rate slow enough such that the reaction temperature did not exceed −18° C. highly exothermic, ca. 20 minutes). TLC analysis of the reaction mixture 10 minutes post peracetic acid addition indicated that conversion of the aldehyde was complete. The reaction solution was then treated with a 0.1M aqueous solution of sodium thiosulfate ($Na_2S_2O_3$, 11 mL). A sample (0.5 mL) was withdrawn from the organic layer for GC analysis. The reactor contents were transferred to a separatory funnel using n-butyl acetate (20 mL), and the butyl acetate layer was washed with water (50 mL). The butyl acetate solution of naproxen acid was then extracted with two portions of a 5% aqueous solution of sodium hydroxide (NaOH, 30 mL each). The combined NaOH solutions of sodium naproxenate were acidified with stirring to pH=1 with a 5% aqueous solution of hydrochloric acid (65 mL), precipitating the naproxen acid. The mixture was vacuum filtered through a #1 Whatman filter. The white solid thus obtained was dried in a vacuum oven 14 hours at 55° C. (25 mm Hg), giving 0.804 g (74.7%, not including withdrawn sample; 85% corrected for withdrawn sample) of naproxen. Chiral phase HPLC analysis indicated a ratio of S:R naproxen of 88.7:11.3 (77.4%ee), the same ratio as the starting aldehyde within experimental error.

EXAMPLE 21

Oxidation Of (S)-2-(6-Methoxy-2-naphthyl) propionaldehyde To S-Naproxen With Peracetic Acid (1.5 Equivalents) Using 4-Methylmorpholine N-Oxide (1.0 Equivalent)/Acetic Acid (1.0 Equivalent) As Catalyst To a stirred solution of 3.0 g (14.0 mmol) of(S)-2-(6-methoxy-2-naphthyl)propionaldehyde (ca. 94% pure by GC) in n-butyl acetate (14.0 mL) cooled in a wet-ice bath (ca. 2° C.) was added 0.84 g (14.0 mmol) of glacial acetic acid followed by 1.64 g (14.0 mmol) of 4-methylmorpholine N-oxide. To this solution was then added slowly dropwise 7.7 mL (21.0 mmol) of a 23.0 weight percent solution of peracetic acid in ethyl acetate, at a rate slow enough such that the reaction temperature did not exceed 5° C. The reaction mixture was stirred at 2° C. for 4 hours, then excess peracetic acid was neutralized by the addition of a 1.0M aqueous solution of sodium thiosulfate ($Na_2S_2O_3$, 10 mL). The solution was transferred into a separatory funnel with the aid of n-butyl acetate (25 mL), and the aqueous layer was separated and discarded. The butyl acetate solution of naproxen acid was then extracted with two portions of a 5% aqueous solution of sodium hydroxide (NaOH, 50 mL each). The combined NaOH solutions of sodium naproxenate were acidified with stirring to pH=2 with a 5% aqueous solution of hydrochloric acid (100 mL), precipitating the naproxen acid. The mixture was cooled in a wet-ice bath and was vacuum filtered through a #2 Whatman filter. The white solid thus obtained was dried in a vacuum oven 14 hours at 5° C. (25 mm Hg), giving 2.58 g (80.0%) of naproxen. Chiral phase HPLC analysis indicated a ratio of S: R naproxen of 78.0:22.0 (partial racemization; this batch of aldehyde was known to give acid with S:R content of 88.1:21.9).

EXAMPLE 22

Oxidation Of (S)-2-(6-Methoxy-2-naphthyl) propionaldehyde To S-Naproxen With Peracetic Acid (3.0 Equivalents) Using Triethanolamine (1.0 Equivalent)/Acetic Acid (1.0 Equivalent) As Catalyst To a stirred solution of 1.0 g (4.67 mmol) of (S)-2-(6-methoxy-2-naphthyl)propionaldehyde in absolute ethanol (5.0 mL) cooled in a wet-ice bath (ca. 2° C.) was added 0.27 mL (0.28 g, 4.67 mmol) of glacial acetic acid followed by 0.62 mL (0.70 g, 4.67 mmol) of triethanolamine. To this solution was then added slowly dropwise 2.25 mL (7.0 mmol) of a 23.0 weight percent solution of peracetic acid in ethyl acetate, at a rate slow enough such that the reaction temperature did not exceed 10° C. The reaction mixture was stirred at 2° C. for 2 hours, then an additional 2.25 mL (7.0 mmol) of the peracetic acid solution was added to complete the conversion of the aldehyde (4 hours total). The solution was transferred into a larger flask with the aid of ethanol (5 mL), heated to 50° C., and was diluted with water (40 mL). The solution was cooled in a wet-ice bath causing precipitation, and was vacuum filtered through a #2 Whatman filter. The light purple solid thus obtained was washed with 20 mL water and was dried in a vacuum oven 14 hours at 55° C. (25 mm Hg), giving 0.79 g (73.5%) of naproxen. Chiral phase HPLC analysis indicated a ratio of S:R naproxen of 95.8: 4.2, the same as that obtained by an independent oxidation method.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

We claim:

1. A process for producing an optically active carboxylic acid which process comprises oxidizing an optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid, wherein said amine and/or amine N-oxide catalyst has a basicity sufficient to catalyze said oxidizing of the optically active aldehyde to the optically active carboxylic acid.

2. The process of claim 1 which is conducted in the presence of a weak organic acid.

3. The process of claim 1 in which the optically active aldehyde is selected from S-2-(p-isobutyl-phenyl) propionaldehyde, S-2-(6-methoxy-2-naphthyl) propionaldehyde, S-2-(3-benzoylphenyl)propionaldehyde, S-2-(p-thienoylphenyl)-propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(3-phenoxy) propionaldehyde, S-2-phenylbutyraldehyde, S-2-(4-isobutylphenyl)butyraldehyde, S-2-phenoxypropionaldehyde, S-2-chloropropionaldehyde, R-2-(3-benzoylphenyl)propionaldehyde and R-2-(3-fluoro-4-phenyl)phenylpropionaldehyde.

4. The process of claim 1 in which the peracid is selected from peracetic acid, performic acid, perpropionic acid and perbenzoic acid.

5. The process of claim 1 in which the amine and/or amine N-oxide catalyst is selected from 2,6-lutidine N-oxide, 5-ethyl-2-methylpyridine, 5-ethyl-2-methylpyridine N-oxide, 4-methoxypyridine N-oxide and 2,5-lutidine N-oxide.

6. The process of claim 1 in which the optically active carboxylic acid is selected from S-2-(p-isobutylphenyl)

propionic acid, S-2-(6-methoxy-2-naphthyl)propionic acid, S-2-(3-benzoylphenyl)propionic acid, S-2-(p-thienoylphenyl)propionic acid, S-2-(3-fluoro-4-phenyl)phenylpropionic acid, S-2-[4-(1,3-dihydro-1-oxo-2H-isoindol-2-yl)phenyl]propionic acid, S-2-(3-phenoxy)propionic acid, S-2-phenylbutyric acid, S-2-(4-isobutylphenyl)butyric acid, S-2-phenoxypropionic acid, S-2-chloropropionic acid, R-2-(3-benzoylphenyl)propionic acid and R-2-(3-fluoro-4-phenyl)-phenylpropionic acid.

7. The process of claim 1 in which the optically active aldehyde is produced by asymmetric hydroformylation, asymmetric olefin isomerization or asymmetric aldol condensation.

8. A process for producing an optically active carboxylic acid which process comprises: (1) reacting a prochiral or chiral olefinically unsaturated organic compound with carbon monoxide and hydrogen in the presence of an optically active metal-ligand complex catalyst to produce an optically active aldehyde; and (2) oxidizing the optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof to produce the optically active carboxylic acid, wherein said amine and/or amine N-oxide catalyst has a basicity sufficient to catalyze said oxidizing of the optically active aldehyde to the optically active carboxylic acid.

9. The process of claim 8 in which said optically active metal-ligand complex catalyst comprises a metal selected from a Group VIII, Group IB, Group VIB and Group VA metal complexed with an optically active ligand having the formula:

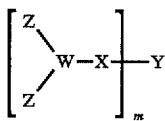

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active.

10. The process of claim 8 in which the prochiral or chiral compound is selected from p-isobutylstyrene, 2-vinyl-6-methoxynaphthylene, 3-ethenylphenyl phenyl ketone, 4-ethenylphenyl 2-thienyl ketone, 4-ethenyl-2-fluorobiphenyl, 4-(1,3-dihydro-1-oxo-2H-isoindol-2-yl)styrene, 2-ethenyl-5-benzoylthiophene, 3-ethenylphenyl phenyl ether, propenylbenzene, isobutyl-4-propenylbenzene, phenyl vinyl ether and vinyl chloride.

11. The process of claim 8 in which the optically active aldehyde is selected from S-2-(p-isobutyl-phenyl)propionaldehyde, S-2-(6-methoxy-2-naphthyl)propionaldehyde, S-2-(3-benzoylphenyl)propionaldehyde, S-2-(p-thienoylphenyl)-propionaldehyde, S-2-(3-fluoro-4-phenyl)phenylpropionaldehyde, S-2-[4-(1,3-dihydro-1-oxo-2H-isoindol-2-yl)phenyl]propionaldehyde, S-2-(3-phenoxy)propionaldehyde, S-2-phenylbutyraldehyde, S-2-(4-isobutylphenyl)butyraldehyde, S-2-phenoxypropionaldehyde, S-2-chloropropionaldehyde, R-2-(3-benzoylphenyl)propionaldehyde and R-2-(3-fluoro-4-phenyl)phenylpropionaldehyde.

12. The process of claim 8 in which the peracid is selected from peracetic acid, performic acid, perpropionic acid and perbenzoic acid.

13. The process of claim 8 in which the amine and/or amine N-oxide catalyst is selected from 2,6-lutidine N-oxide, 5-ethyl-2-methylpyridine, 5-ethyl-2-methylpyridine N-oxide, 4-methoxypyridine N-oxide and 2,5-lutidine N-oxide.

14. The process of claim 8 in which the optically active carboxylic acid comprises S-2-(p-isobutylphenyl)propionic acid, S-2-(6-methoxy-2-naphthyl)propionic acid, S-2-(3-benzoylphenyl)propionic acid, S-2-(p-thienoylphenyl)propionic acid, S-2-(3-fluoro-4-phenyl)phenylpropionic acid, S-2-[4-(1,3-dihydro-1-oxo-2H-isoindol-2-yl)phenyl]propionic acid, S-2-(3-phenoxy)propionic acid, S-2-phenylbutyric acid, S-2-(4-isobutylphenyl)butyric acid, S-2-phenoxypropionic acid, S-2-chloropropionic acid, R-2-(3-benzoylphenyl)propionic acid or R-2-(3-fiuoro-4-phenyl)-phenylpropionic acid.

15. A process for producing an optically active carboxylic acid which process comprises: (1) reacting a prochiral or chiral olefinically unsaturated organic compound with carbon monoxide and hydrogen in the presence of an optically active rhodium-ligand complex catalyst to produce an optically active aldehyde; and (2) oxidizing the optically active aldehyde with a peracid in the presence of an amine and/or amine N-oxide catalyst selected from the group consisting of a substituted or unsubstituted alkyl amine, alkyl amine N-oxide, aromatic amine, aromatic amine N-oxide, heterocyclic amine, heterocyclic amine N-oxide and mixtures thereof, to produce the optically active carboxylic acid, wherein said amine and/or amine N-oxide catalyst has a basicity sufficient to catalyze said oxidizing of the optically active aldehyde to the optically active carboxylic acid.

16. The process of claim 15 in which said optically active rhodium-ligand complex catalyst comprises rhodium complexed with an optically active ligand having the formula:

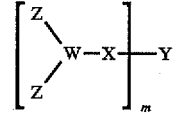

wherein each W is the same or different and is phosphorus, arsenic or antimony, each X is the same or different and is oxygen, nitrogen or a covalent bond linking W and Y, Y is a substituted or unsubstituted hydrocarbon residue, each Z is the same or different and is a substituted or unsubstituted hydrocarbon residue or the Z substituents bonded to W may be bridged together to form a substituted or unsubstituted cyclic hydrocarbon residue, and m is a value equal to the free valence of Y, provided at least one of Y and Z is optically active.

17. The process of claim 16 in which the optically active ligand is (2R,4R)-di[2,2'-(3,3'-di-tert-butyl-5,5'-dimethoxy-1,1-biphenyl)]-2,4-pentyl diphosphite.

18. The process of claim 16 in which the optically active rhodium-ligand complex catalyst comprises rhodium complexed with an optically active ligand having the formula selected from:

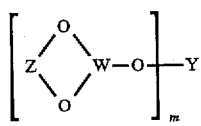

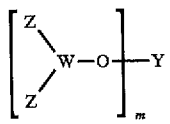

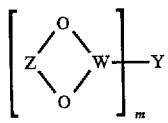

-continued

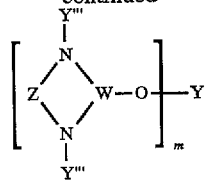

wherein W, Y, Z and m are as defined in claim 16 and Y'" is the same or different and is hydrogen or a substituted or unsubstituted hydrocarbon residue.

19. The process of claim 15 in which the amine and/or amine N-oxide catalyst is selected from 2,6-lutidine N-oxide, 5-ethyl-2-methylpyridine, 5-ethyl-2-methylpyridine N-oxide, 4-methoxypyridine N-oxide and 2,5-lutidine N-oxide.

* * * * *